US011041841B2

(12) United States Patent
Niemann

(10) Patent No.: US 11,041,841 B2
(45) Date of Patent: Jun. 22, 2021

(54) SOIL MOISTURE DOWNSCALING USING TOPOGRAPHY, SOIL, AND VEGETATION DATA

(71) Applicant: Colorado State University Research Foundation, Fort Collins, CO (US)

(72) Inventor: Jeffrey D. Niemann, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 357 days.

(21) Appl. No.: 15/769,049

(22) PCT Filed: Oct. 19, 2016

(86) PCT No.: PCT/US2016/057687
§ 371 (c)(1),
(2) Date: Apr. 17, 2018

(87) PCT Pub. No.: WO2017/070199
PCT Pub. Date: Apr. 27, 2017

(65) Prior Publication Data
US 2019/0049422 A1 Feb. 14, 2019

Related U.S. Application Data

(60) Provisional application No. 62/244,970, filed on Oct. 22, 2015.

(51) Int. Cl.
*G01N 33/24* (2006.01)
*G01W 1/00* (2006.01)

(52) U.S. Cl.
CPC ............ *G01N 33/246* (2013.01); *G01W 1/00* (2013.01)

(58) Field of Classification Search
CPC .............................. G01N 33/246; G01W 1/00
(Continued)

(56) References Cited

U.S. PATENT DOCUMENTS 7,804,309 B2 9/2010 Cummins
2012/0284264 A1 11/2012 Lankford et al.
2016/0302351 A1* 10/2016 Schildroth ............ B64C 39/024

FOREIGN PATENT DOCUMENTS

CN 102354348 A * 2/2012
WO 2014186810 A1 11/2014

OTHER PUBLICATIONS

Kevin L. Werbylo, Jeffrey D. Niemann, Evaluation of sampling techniques to characterize topographically-dependent variability for soil moisture downscaling, Jan. 21, 2014, Journal of Hydrology, 516 (2014) 304-316, pp. 304-316 (Year: 2014).*
(Continued)

*Primary Examiner* — Eman A Alkafawi
(74) *Attorney, Agent, or Firm* — Maschoff Brennan; Paul G. Johnson

(57) ABSTRACT

Systems and methods are disclosed to downscale the resolution of a coarse-resolution soil moisture data. Coarse-resolution soil moisture data may include data cells that each represent a geographic region having at least one dimension greater than or equal to 1 km. A plurality of fine-resolution supplemental soil moisture data may be received that includes at least one of soil data, vegetation data, topography data, and climate data. The fine-resolution supplemental soil moisture data comprising data cells that each represent a geographic region having at least one dimension less than or equal to 100 meters. The coarse-resolution soil moisture data may be downscaled to fine-resolution soil moisture data using the plurality of fine-resolution supplemental soil moisture data, the fine-resolution soil moisture data comprising
(Continued)

data cells that each represent a geographic region having at least one dimension less than 100 meters.

14 Claims, 15 Drawing Sheets

(58) Field of Classification Search
USPC .............................................................. 702/5
See application file for complete search history.

(56) References Cited

OTHER PUBLICATIONS

Michael L. Coleman and Jeffrey D. Niemann, An evaluation of nonlinear methods for estimating catchment-scale soil moisture patterns based on topographic attributes, 2012, Journal of Hydormatics 14.3 2012, pp. 800-814. (Year: 2012).*

Translation of CN102354348A, Watershed scale soil moisture remote sensing assimilation method. Joingfeng Chen, Wanchang Zhang, Feb. 15, 2012 (Year: 2012).*

Michael L. Coleman , Jeffrey D. Niemann, "Controls on topographic dependence and temporal instability in catchment-scale soil moisture patterns", Feb. 26, 2013, Water Resources Research /vol. 49, Issue 3, pp. 1-40/40. (Year: 2013).*

Ranney et al. "A Moment to downscale soil moisture to fine resolutions using topographic vegetation, and soil data" Thesis, Dec. 3, 2014, 79 pages.

International Search Report and Written Opinion from PCT Application No. PCT/US2016/57687 dated Jan. 17, 2017, 33 pages.

Ranney et al.; "A Method to Downscale Soil Moisture to Fine Resolutions Using Topographic, Vegetation, and Soil Data"; Advances in Water Resources; 2015; vol. 76; pp. 81-96; ISBN 0309-1708; 16 pages.

* cited by examiner 0.04   0.16   0.27

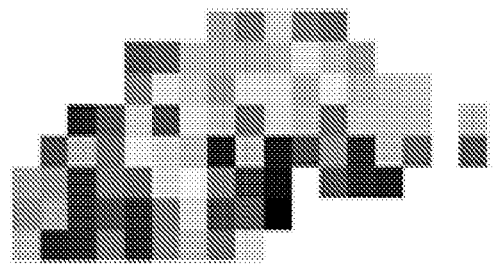
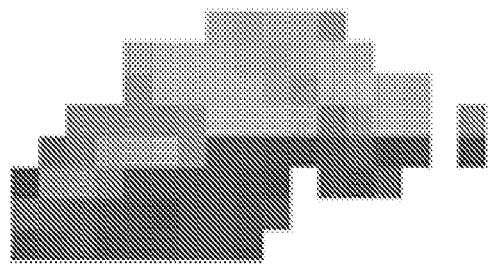
FIG. 12A            FIG. 12B
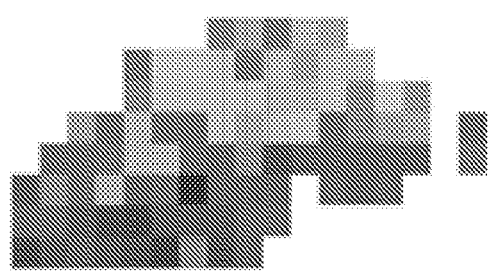
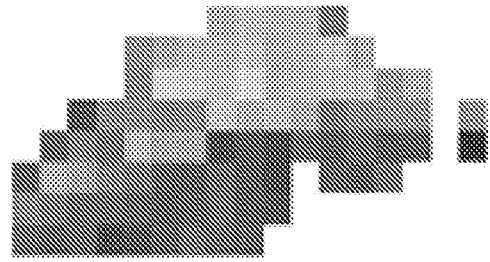
FIG. 12C            FIG. 12D
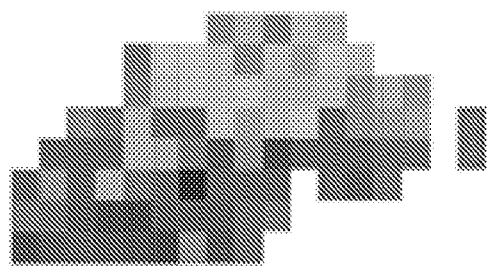
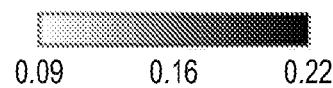
0.09    0.16    0.22
FIG. 12E

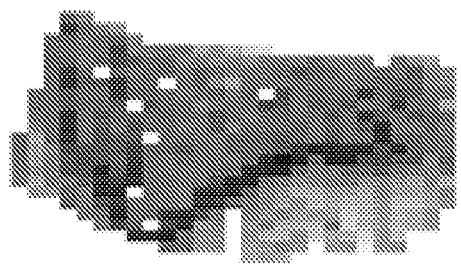 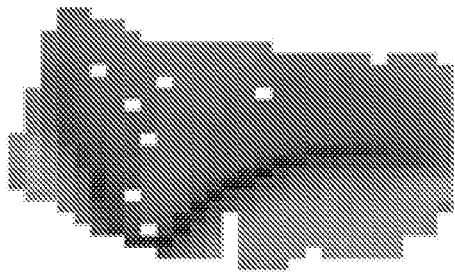
FIG. 13A              FIG. 13B
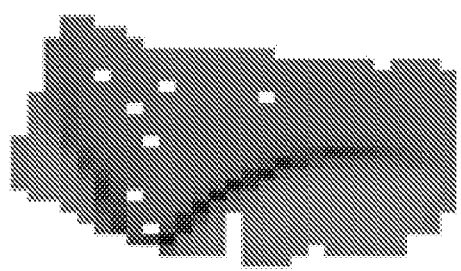 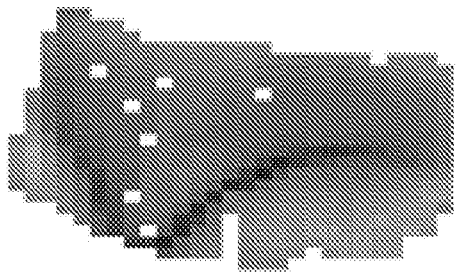
FIG. 13C              FIG. 13D
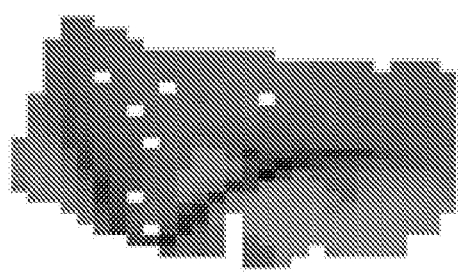
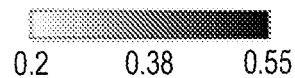
0.2    0.38   0.55
FIG. 13E

SOIL MOISTURE DOWNSCALING USING TOPOGRAPHY, SOIL, AND VEGETATION DATA

CROSS-REFERENCE

This application is a PCT Application claiming priority benefit of U.S. provisional patent application Ser. No. 62/244,970, filed on Oct. 22, 2015, titled "Equilibrium Moisture from Topography, Vegetation, and Soil (EMT+VS) Downscaling Method," the entire disclosure of which is herein incorporated by reference for all purposes.

GOVERNMENT RIGHTS

This invention was made with government support under grant W911NF-11-1-0438 awarded by Army Research Office. The government has certain rights in the invention.

BACKGROUND

Soil moisture can be estimated over large regions with spatial resolutions greater than 500 m. Several methods have been used to downscale coarse-resolution soil moisture data, but with poor performance.

SUMMARY

Systems and methods are disclosed to downscale the resolution of coarse-resolution soil moisture data. In some embodiments, coarse-resolution soil moisture data can be received. The coarse-resolution soil moisture data may be comprised of data cells that represent a geographic region having at least one dimension greater than or equal to 1 km. A plurality of fine-resolution supplemental soil moisture data may be received that includes at least one of soil data, vegetation data, topography data, and climate data. The fine-resolution supplemental soil moisture data may be comprised of data cells that represent a geographic region having at least one dimension less than or equal to 100 meters. The coarse-resolution soil moisture data may be downscaled to fine-resolution soil moisture data using the plurality of fine-resolution supplemental soil moisture data, the fine-resolution soil moisture data comprising data cells that represent a geographic region having at least one dimension less than or equal to 100 meters.

These illustrative embodiments are mentioned not to limit or define the disclosure, but to provide examples to aid understanding thereof. Additional embodiments are discussed in the Detailed Description, and further description is provided. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

FIG. 12A illustrates the observed soil moisture pattern at Cache la Poudre on a date with intermediate moisture.

FIG. 12B illustrates an estimated soil moisture pattern at Cache la Poudre using the EOF model with fine-resolution topography and vegetation information.

FIG. 12C illustrates an estimated soil moisture pattern at Cache la Poudre using the EMT+VS model with fine-resolution topography and vegetation information.

FIG. 12D illustrates an estimated soil moisture pattern at Cache la Poudre using the EOF model with fine-resolution topography, vegetation, and soil information.

FIG. 12E illustrates an estimated soil moisture pattern at Cache la Poudre using the EMT+VS model with fine-resolution topography, vegetation, and soil information.

FIG. 13A illustrates the observed soil moisture pattern at Tarrawarra with intermediate moisture.

FIG. 13B illustrates an estimated soil moisture pattern at Tarrawarra using the EOF model with fine-resolution topography information.

FIG. 13C illustrates an estimated soil moisture pattern at Tarrawarra using the EMT+VS model with fine-resolution topography information.

FIG. 13D illustrates an estimated soil moisture pattern at Tarrawarra using the EOF model with fine-resolution topography and soil information.

FIG. 13E illustrates an estimated soil moisture pattern at Tarrawarra using the EMT+VS model with fine-resolution topography and soil information.

DETAILED DESCRIPTION

In some embodiments, systems and methods are disclosed for estimating the soil moisture with fine-resolution within a geographic region of interest from coarse-resolution soil moisture data of the geographic region of interest and fine-resolution data regarding the topography, vegetation, and/or soil within the region of interest.

In some embodiments, systems and methods are disclosed for downscaling coarse-resolution soil moisture data within a geographic region of interest using fine-resolution topography, vegetation, climate, and/or soil data within the geographic region of interest. In some embodiments, downscaling can improve the spatial resolution of the soil moisture data.

In some embodiments, vegetation data may include the vegetation's role in interception, transpiration, climate, and/or soil evaporation. In some embodiments, either or both vegetation and soil properties may vary at fine-resolution.

In some embodiments, coarse-resolution may refer to a special resolution within a region of interest that is greater than about 1 km, 5 km, 10 km, 50 km, 100 km, 500 km, etc. In some embodiments, fine-resolution may refer to a spatial resolution within a region of interest that is less than about 100 m, 50 m, 10 m, 5 m, 1 m, etc.

Various embodiments of the invention are described in this disclosure that outline a model for downscaling soil moisture data, which may be referred to generally as the model or the Equilibrium Moisture from Topography, Vegetation, and Soil model (EMT+VS model). A number of variations of EMT+VS model are disclosed and include a number of variations thereof.

Figure 1:
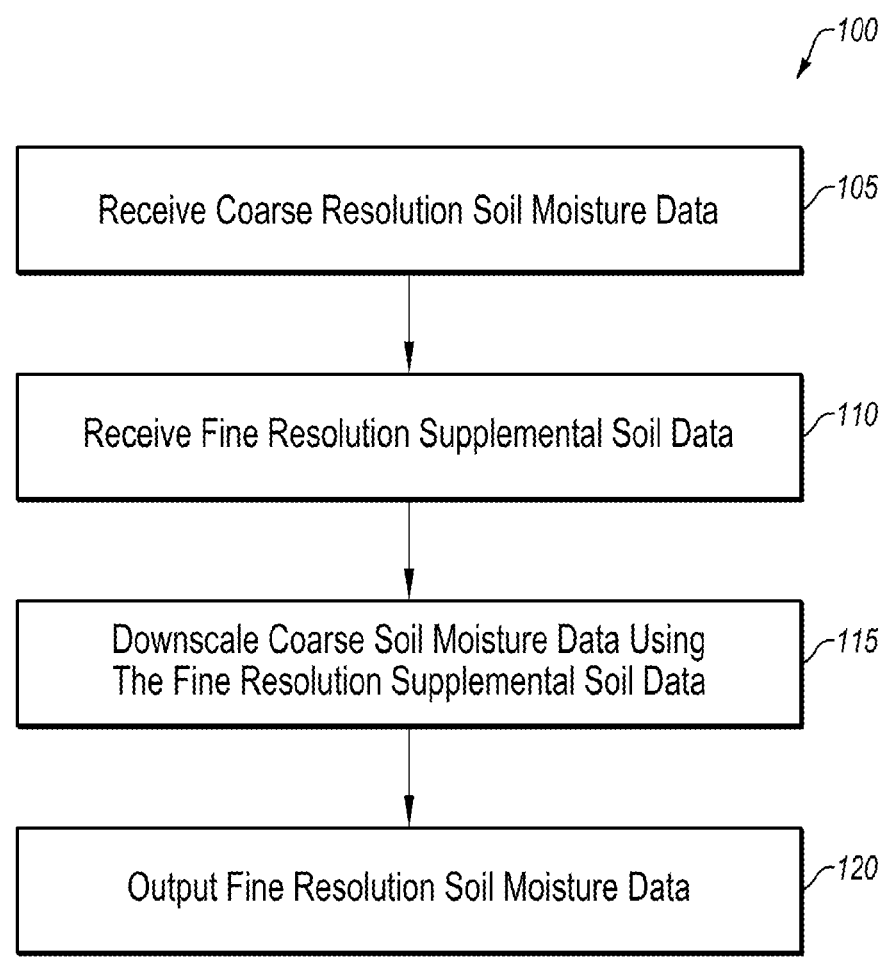
FIG. 1 is an example flowchart of process according to some embodiments.

FIG. 1 is an example flowchart of a process 100 according to some embodiments. Process 100 may produce fine-resolution soil moisture data from coarse-resolution soil moisture data using the EMT+VS model. In some embodiments, process 100 may be executed by computational unit 1500 shown in FIG. 15.

Process 100 may begin at block 105. At block 105, coarse-resolution soil moisture data may be received for a geographic area. In some embodiments, the coarse-resolution soil moisture data may include soil moisture data from the Advanced Microwave Scanning Radiometer (AMSR-E), the Soil Moisture and Ocean Salinity (SMOS), WindSat, and/or the Soil Moisture Active Passive (SMAP) satellites, etc. In some embodiments, the coarse-resolution soil moisture data may include soil moisture data created from computer models such as, for example, land surface components of weather forecasting and analysis models such as AGRMET and Noah. In some embodiments, the coarse-resolution soil moisture data may include soil moisture values with resolutions greater than about 1 km, 5 km, 10 km, 50 km, 100 km, 500 km, etc. For example, the coarse-resolution soil moisture data may include a plurality of grid cells that each represent a soil moisture value for a corresponding grid cell within the geographic region of interest.

Figure 15:
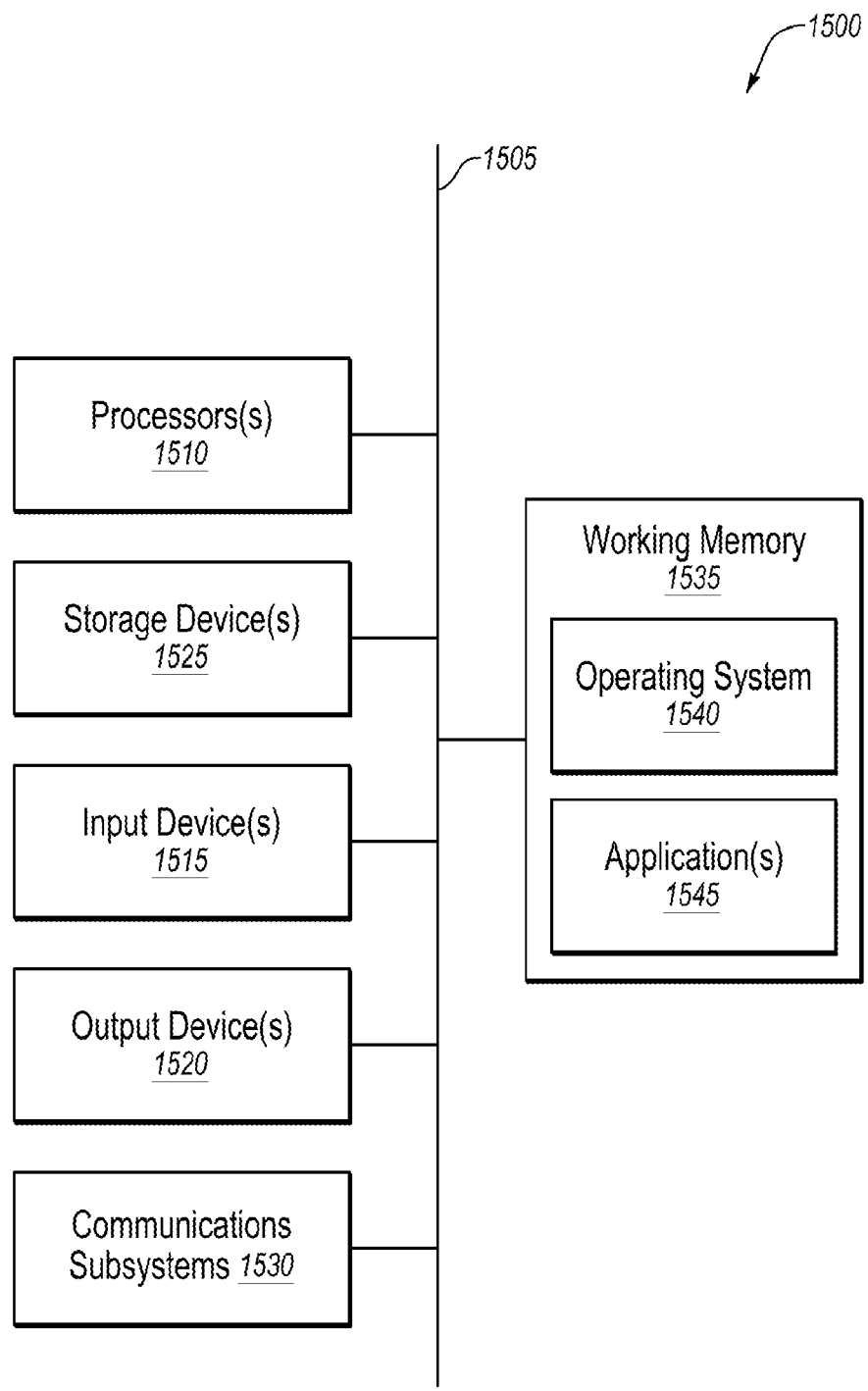
FIG. 15 shows an illustrative computational system for performing functionality to facilitate implementation of embodiments described herein.

In some embodiments, the coarse-resolution soil moisture data may be received at the computational system 1500 of FIG. 15 through a network interface such as, for example, input device 1515, from a network location through the Internet.

In some embodiments, the coarse-resolution soil moisture data may be stored within a storage location within the computational system 1500 such as, for example, storage devices 1525.

At block 110 fine-resolution supplemental soil moisture data may be received according to some embodiments. The fine-resolution supplemental soil moisture data may include data representing the topography of the geographic region, the vegetation within the geographic region, the soil conditions within the geographic region, and/or the climate within the geographic region, etc.

In some embodiments, the data representing the topography of the geographic region (e.g., topography parameters) may include data representing the elevation, the area that is upslope from the edge of a coarse-resolution cell or a fine-resolution cell, the topographic slope, the topographic curvature, and/or the potential solar radiation index (PSRI)

(e.g., the ratio of the insolation of the topographic surface to that of a horizontal surface at the same latitude and date), etc. In some embodiments, the topography of the geographic region may include data representing a coarse-resolution or a fine-resolution cell. In some embodiments, one or more of the topography parameters may vary spatially.

In some embodiments, the data representing the vegetation within the geographic region (e.g., vegetation parameters) may include the fractional vegetation cover, and/or one or more parameters that depend on the type of vegetation, land cover, etc. In some embodiments, the data representing the vegetation may include data representing a coarse-resolution or a fine-resolution cell. In some embodiments, one or more of the vegetation parameters may vary spatially.

In some embodiments, the data representing the soil conditions within the geographic region (e.g., soil condition parameters) may include the porosity of the soil, the vertical saturated hydraulic conductivity, the horizontal saturated hydraulic conductivity, the anisotropy of saturated hydraulic conductivity, the thickness of the hydrologically active layer where the topographic curvature is zero, the minimum topographic curvature, and/or parameter that relates the horizontal hydraulic gradient to topographic slope, etc. In some embodiments, the data representing the soil conditions may include data representing a coarse-resolution or a fine-resolution cell. In some embodiments, one or more of the soil condition parameters may vary spatially. In some embodiments, the data representing the soil conditions within the geographic region may be derived from soil texture parameters such as, for example, the percentage of sand, slit, and/or clay within the soil.

In some embodiments, the data representing the climate within the geographic region (e.g., climate parameters) may include the potential and/or reference crop evapotranspiration, and/or the ratio of the aerodynamic term to the radiation term (i.e. the Priestly-Taylor coefficient minus one), wind speed, etc. In some embodiments, the data representing the climate within the geographic region may include data representing a coarse-resolution or a fine-resolution cell. In some embodiments, one or more of the climate parameters may vary spatially.

In some embodiments, the fine-resolution soil data may include the deep drainage index (DDI), the lateral flow index (LFE), the radiative evapotranspiration (ET) index (REI), and/or the aerodynamic ET index (AEI). Examples of these indices are provided below. The DDI, LFI, REI, and/or the AEI, for example, may introduce fine scale variability in the soil moisture pattern, may represent a compound index that may include vegetation, soil, topographic, and/or climatic characteristics. In some embodiments, the fine-resolution soil data may include a spatial average of the DDI, LFI, REI, and/or the AEI at coarse or fine resolutions. The DDI, LFI, REI, and/or the AEI for example, may vary spatially.

In some embodiments, the fine-resolution supplemental soil moisture data may be received at the computational system 1500 through a network interface such as, for example, input device 1515, from a network location through the Internet.

In some embodiments, the fine-resolution supplemental soil moisture data may be stored within a storage location within the computational system 1500 such as, for example, storage devices 1525.

At block 115 the coarse-resolution soil moisture data may be downscaled to fine-resolution soil moisture data using the supplemental soil moisture data. In some embodiments, the coarse-resolution soil moisture data may be downscaled to fine-resolution soil moisture data using the computational system 1500. In some embodiments, the coarse-resolution soil moisture data may be downscaled to fine-resolution soil moisture data using the equations described below.

In some embodiments, the coarse-resolution soil moisture data may be downscaled to fine-resolution soil moisture data using a weighted average of soil moisture estimates that are determined from the various supplemental soil moisture data. For example, the following equation can be used to calculate the soil moisture for each fine resolution cell in a digital elevation model:

$$\theta = \frac{w_G \theta_G + w_L \theta_L + w_R \theta_R + w_A \theta_A}{w_G + w_L + w_R + w_A} \quad (1)$$

where:

$$w_G = \left(\frac{\overline{\theta}}{\Psi}\right)^{\gamma_v} \quad (2)$$

$$w_L = \left(\frac{\overline{\theta}}{\Lambda}\right)^{\gamma_h} \quad (3)$$

$$w_R = \left(\frac{\overline{\theta}}{\Pi}\right)^{\beta_r} \quad (4)$$

$$w_A = \left(\frac{\overline{\theta}}{\Omega}\right)^{\beta_a} \quad (5)$$

$$\theta_A = \overline{\theta}\frac{AEI}{\Omega} \quad (6)$$

$$\theta_R = \overline{\theta}\frac{REI}{\Pi} \quad (7)$$

$$\theta_L = \overline{\theta}\frac{LFI}{\Lambda} \quad (8)$$

$$\theta_G = \overline{\theta}\frac{DDI}{\Psi}. \quad (9)$$

$\overline{\theta}$ represents the spatial-average soil moisture typically within a specified spatial extent around the grid cell or a coarse-resolution grid cell such as, for example, the spatial-average soil moisture within a cell of the coarse-resolution soil moisture data received at block 105. In some embodiments, the DDI, LFI, REI, and/or AEI may introduce fine scale variability in the soil moisture pattern. In some embodiments, the DDI, LFI, REI, and/or AEI may represent a compound index that may include vegetation, soil, topographic, and/or climatic characteristics. In some embodiments, the DDI, LFI, REI, and/or AEI may include data at the fine or coarse resolution. Various equations and/or values may be used to represent these parameters. Example equations for the DDI, LFI, REI, and AEI are shown below. In some embodiments, other indices may be used such as, for example, radiative evaporation, radiative transpiration, aerodynamic evaporation, and aerodynamic transpiration. In some embodiments, the DDI, LFI, REI, and AEI may be determined for each fine-resolution grid cell. Various equations and/or values may be used to represent these values.

$\Psi$ represents the spatial-average DDI typically within a specified spatial extent around the fine resolution grid cell or the extent of the coarse-resolution grid cell, $\Lambda$ is the spatial-average lateral flow index (LFI) typically within a specified spatial extent around the fine resolution grid cell or the extent of the coarse-resolution grid cell, $\Pi$ is the spatial-average radiative ET index (REI) typically within a specified spatial extent around the fine resolution grid cell or the extent of the coarse-resolution grid cell, and Ω denotes the spatial-average aerodynamic ET index (AEI) typically within a specified spatial extent around the fine resolution grid cell or the extent of the coarse-resolution grid cell. $\beta_r$ and $\beta_a$ are parameters to describe the effects of limited soil moisture on ET and depend on the soil and/or vegetation type within a given coarse or fine resolution grid cell, $\gamma_h$ is the horizontal pore disconnectedness index within a given coarse or fine resolution grid cell, which depends on the soil type, and $\gamma_v$ is the vertical pore disconnectedness index within a given coarse or fine resolution grid cell, which depends on the soil type. Various equations and/or values may be used to represent these values.

In some embodiments, one or more of $w_G$, $w_L$, $w_R$, and/or $w_A$ may be zero for one or more fine-resolution cells or one or more times for which the soil moisture is being generated.

At block 120 the fine-resolution soil moisture data may be output. For example, the fine-resolution soil moisture data may be output as a matrix of soil moisture values. Outputs may also include polygons representing different soil moisture values, locations that are identified saturated or ponded, depth of ponded water or runoff, degree of saturation at each location, and/or measures of the likelihood of saturation/ponding occurring at any given location. As another example, the fine-resolution soil moisture data may be output in conjunction with a digital elevation model. As another example, the fine-resolution soil moisture data may be output as color values on a map.

Some embodiments of the invention may be considered to simulate a hydrologically active layer. The hydrologically active layer, for example, may be defined as the depth of soil through which lateral flow can occur and/or as the total soil depth. The hydrologically active layer can be considered as beginning at the ground surface and ending at a depth where the hydraulic conductivity decreases due to the occurrence of bedrock or a relatively impermeable soil layer. In some embodiments the hydrologically active layer may be approximated as a selected depth or a depth with available soil moisture measurements. In some embodiments, the model is based on the water balance for the active layer in the land area that is upslope from an edge of a grid cell in a digital elevation model. In some embodiments, soil moisture may be assumed to be uniform with depth in the layer, and/or infiltration may be assumed to be balanced by deep drainage (e.g., groundwater recharge), lateral flow, and/or evapotranspiration. The water balance may be written, for example, as:

$$\int_A FdA = \int_A GdA + L + \int_A EdA \qquad (10)$$

In this equation, A is the area that is upslope from the edge of the digital elevation model cell, F is the infiltration rate, G is the deep drainage, and E is the evapotranspiration for the fine-resolution grid cells included in the upslope area. L is the lateral outflow through the edge of the digital elevation model cell, which is the only location where lateral flow exits the control volume.

In some embodiments, infiltration F can be assumed to be spatially constant. In some embodiments, however, interception may decrease infiltration, so infiltration can be represented as:

$$F = F_{max}(1-\lambda V) \qquad (11)$$

In this equation, $F_{max}$ is the maximum infiltration rate, V is the fractional vegetation cover at the location, and $\lambda$ ($0 \leq \lambda \leq 1$) is a temporally-constant interception efficiency, a parameter that can be used, in some examples, to account for factors that influence interception, such as the foliage holding capacity, which may depend on vegetation and climatic characteristics. In some embodiments, $F_{max}$ may also represent the spatial average participation over a number of cells and/or a local precipitation value within a given cell. In some embodiments, the local precipitation may be determined from topographic characteristics such as elevations, slopes, and orientations that are inferred from the digital elevation model.

In some embodiments, the deep drainage G can be assumed to occur by gravity drainage with no capillary gradient; In some embodiments, deep drainage G can be determined in part from the Campbell equation implying:

$$G = K_{s,v}\left(\frac{\theta}{\phi}\right)^{\gamma_v} \qquad (12)$$

where $K_{s,v}$ is the saturated vertical hydraulic conductivity, $\theta$ is the volumetric soil moisture in the hydrologically active layer, $\phi$ is the porosity, and $\gamma_v$ is the vertical pore disconnectedness index.

In some embodiments, the lateral flow can be derived from one of many perspectives. In one approach, for example, the lateral flow can be assumed to occur throughout the entire unsaturated hydrologically active layer. The flow can then be derived from Darcy's law, where the Campbell equation can be used to calculate the unsaturated horizontal hydraulic conductivity. The horizontal hydraulic gradient, for example, can be assumed to be a power function of the topographic slope, and/or the layer thickness is assumed to depend on the topographic curvature, which has been observed for total soil depth. In another approach, for example, the lateral flow can be assumed to occur in a saturated portion of the hydrologically active layer, where that portion is determined by the depth-averaged degree of saturation in the layer to a power. The flow can then be derived from Darcy's Law using the saturated hydraulic conductivity and the thickness of the saturated layer. In some embodiments, these approaches may lead to the following expression:

$$L = \delta_0\left(\frac{\kappa_{min} - \kappa}{\kappa_{min}}\right)c \iota K_{s,v}\left(\frac{\theta}{\phi}\right)^{\gamma_h} S^\varepsilon \qquad (13)$$

where $\delta_0$ is the thickness of the hydrologically active layer where the topographic curvature is zero, $\kappa_{min}$ is the minimum topographic curvature for which the layer is present, and $\kappa$ is the topographic curvature, which can be positive for convergent locations and negative for divergent locations. c is the length of the fine resolution grid-cell edge, a is the anisotropy of saturated hydraulic conductivity (e.g., used to transform $K_{s,v}$ to the horizontal saturated hydraulic conductivity), S is topographic slope, and $\varepsilon$ is a parameter that relates the horizontal hydraulic gradient to topographic slope. $\gamma_h$ is the horizontal pore disconnectedness index if the lateral flow is unsaturated, but it can take smaller values (e.g., closer to one) if the lateral flow occurs in a saturated portion of the layer.

In some embodiments, it can be assumed that the aerodynamic term is a specified fraction of the radiation term in the Penman equation. In some embodiments, the radiation term can be modified to account for the effects of topographic slope and/or aspect and possibly latitude and day of year. To account for moisture limitations, the actual ET may be calculated as the potential ET multiplied by a power function of the degree of saturation. An equation for the ET may be written as:

$$E = E_p[\eta V + (1-V)^\mu]\left[\frac{I_p}{1+\alpha}\left(\frac{\theta}{\phi}\right)^{\beta_r} + \frac{\alpha}{1+\alpha}\left(\frac{\theta}{\phi}\right)^{\beta_a}\right] \quad (14)$$

where $E_p$ is the average potential ET, $I_p$ is the PSRI (e.g., the ratio of the insolation of the topographic surface to that of a horizontal surface at the same latitude and date), $\alpha$ is the ratio of the aerodynamic term to the radiation term (i.e., the Priestly-Taylor coefficient minus one), and $\eta$, $\mu$, $\beta_r$ and $\beta_a$ are parameters that are expected to depend on the vegetation and/or soil characteristics. The first term $$\left(\left[\frac{I_p}{1+\alpha}\left(\frac{\theta}{\phi}\right)^{\beta_r}\right]\right)$$

is the radiative component of the ET, and the second term $$\left(\left[\frac{\alpha}{1+\alpha}\left(\frac{\theta}{\phi}\right)^{\beta_a}\right]\right)$$

is the aerodynamic component of the ET.

Figure 2A:
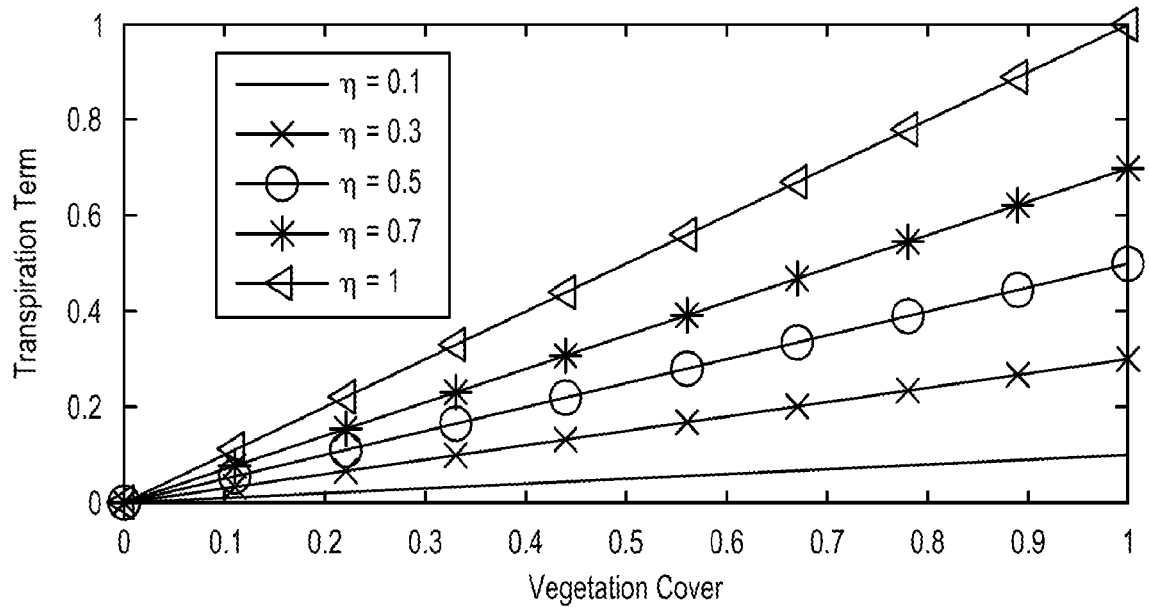
FIG. 2A is a graph of the transpiration in an evapotranspiration equation plotted as a function of vegetation cover using several example parameter values according to some embodiments.

The term $[\eta V+(1-V)^\mu]$ can be derived by partitioning $E_p$ into potential transpiration and potential evaporation according to the fractional vegetation cover V. In the transpiration term $\eta V$, $\eta$ represents the portion of the transpiration that is contributed by the hydrologically active layer. It is expected to depend on the root density in the layer and thus the vegetation type. FIG. 2A shows example behaviors of the transpiration term. The transpiration term can increase, for example, with V because denser vegetation cover is associated with more root-water uptake as shown, for example, in FIG. 2A. The transpiration term can also, for example, increase with $\eta$ because a greater portion of the transpiration is being supplied by the modeled layer.

Figure 2B:
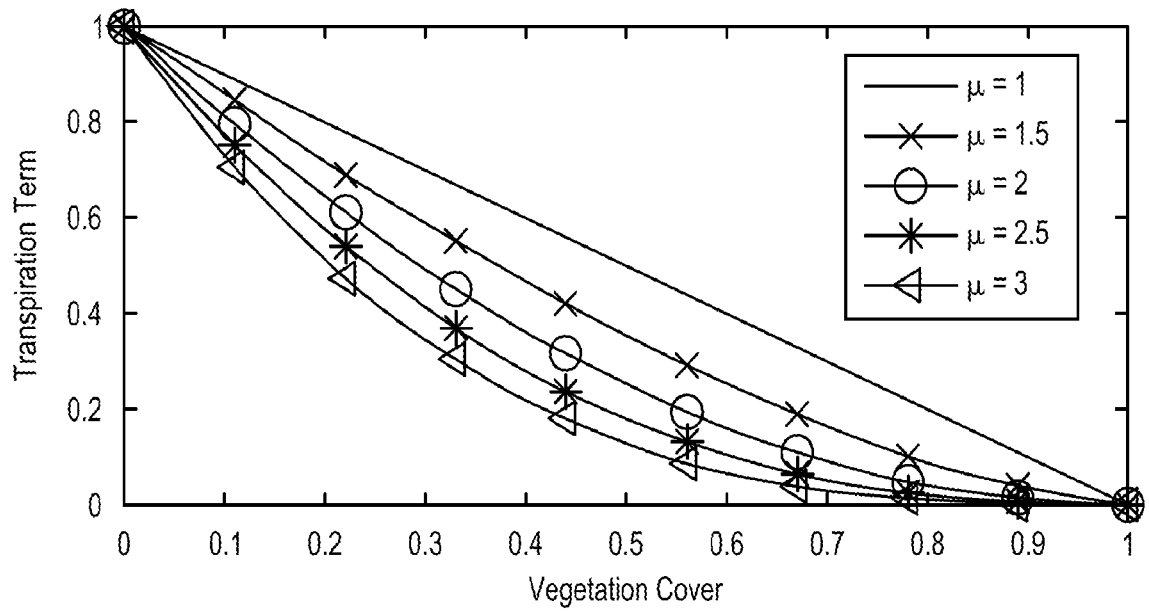
FIG. 2B is a graph of the evaporation term in an evapotranspiration equation plotted as a function of vegetation cover using several example parameter values according to some embodiments.

In the soil evaporation term, $(1-V)^\mu$, the exponent $\mu$ may be introduced because vegetation cover can reduce soil evaporation beyond simply redirecting a portion of the ET to transpiration. Canopy cover can shade the soil surface and reduce the wind speed and humidity gradient near the surface. Litter cover can also shade the surface and retain humidity near it. The evaporation term can decrease as V increases because more of the available energy is used for transpiration as shown, for example, in FIG. 2B. When $\mu$ is larger, the evaporation term is smaller because the vegetation cover also inhibits soil evaporation.

In some embodiments, Equations (11)-(14) are substituted into Equation (10), which produces:

$$F_{max}(1-\lambda V) = \frac{1}{A}\int_A K_{s,v}\left(\frac{\theta}{\phi}\right)^{\gamma_v} dA + \delta_0\left(\frac{\kappa_{min}-\kappa}{\kappa_{min}}\right)\frac{c}{A}\iota K_{s,v}\left(\frac{\theta}{\phi}\right)^{\gamma_h} S^\varepsilon + \quad (15)$$

$$\frac{1}{A}\int_A (\eta V + (1-V)^\mu)\frac{E_p}{(1+\alpha)}I_p\left(\frac{\theta}{\phi}\right)^{\beta_r} dA +$$

$$\frac{1}{A}\int_A (\eta V + (1-V)^\mu)\frac{E_p \alpha}{(1+\alpha)}\left(\frac{\theta}{\phi}\right)^{\beta_a} dA$$

In some embodiments, this expression is approximated by:

$$F_{max}(1-\lambda V) = K_{s,v}\left(\frac{\theta}{\phi}\right)^{\gamma_v} + \delta_0\left(\frac{\kappa_{min}-\kappa}{\kappa_{min}}\right)\frac{c}{A}\iota K_{s,v}\left(\frac{\theta}{\phi}\right)^{\gamma_h} S^\varepsilon + \quad (16)$$

$$\frac{E_p}{(1+\alpha)}(\eta V + (1-V)^\mu)I_p\left(\frac{\theta}{\phi}\right)^{\beta_r} + \frac{E_p \alpha}{(1+\alpha)}(\eta V + (1-V)^\mu)\left(\frac{\theta}{\phi}\right)^{\beta_a}$$

In some embodiments, an explicit equation for $\theta$ can be found, for example, from a weighted average of analytical solutions, which are derived by assuming that each term on the right side of Equation (16) dominates. The soil moisture can, for example, be estimated as:

$$\theta = \frac{w_G \theta_G + w_L \theta_L + w_R \theta_R + w_A \theta_A}{w_G + w_L + w_R + w_A} \quad (17)$$

where $\theta_G$, $\theta_L$, $\theta_R$, and $\theta_A$ are example soil moisture equations of deep drainage, lateral flow, radiative ET, and aerodynamic ET dominate, respectively.

The variables $w_G$, $w_L$, $w_R$, and/or $w_A$ control the importance of $\theta_G$, $\theta_L$, $\theta_R$, and $\theta_A$ to the final estimate of $\theta$ and may be determined from the magnitudes of these four terms in Equations (16).

In some embodiments, a solution can be determined by assuming the other terms are negligible. Starting with the deep drainage term, if the deep drainage term dominates, for example, then the other terms on the right side of Equation (16) can be neglected, which implies:

$$\theta_G = \phi\left[\frac{F_{max}(1-\lambda V)}{K_{s,v}}\right]^{1/\gamma_v} \quad (18)$$

Using this equation, the spatial-average soil moisture $\overline{\theta}$ within a catchment (or a coarse-resolution grid cell) can be determined:

$$\overline{\theta} = \frac{1}{A_c}\int_{A_c} \theta_G dA_c = \frac{F_{max}^{1/\gamma_v}}{A_c}\int_{A_c} \phi\left(\frac{1-\lambda V}{K_{s,v}}\right)^{1/\gamma_v} dA_c \quad (19)$$

where $A_c$ is the catchment (or coarse-resolution grid cell or specified spatial extent's) area.

In this example, $K_{s,v}$ and $\phi$ are allowed to vary within $A_c$ and thus remain inside the integral. In some embodiments, $F_{max}$ and $\gamma_v$ are assumed to be constant. In some embodiments, the term in the integral is a compound vegetation and soil index called the deep drainage index (DDI) denoted as:

$$DDI \equiv \phi\left(\frac{1-\lambda V}{K_{s,v}}\right)^{1/\gamma_v} \quad (20)$$

This equation, for example, can introduce spatial variation into the $\theta$ estimate. If the spatial-average DDI is denoted $\Psi$, Equation (19) can be rewritten as:

$$\overline{\theta} = F_{max}^{1/\gamma_v}\Psi \quad (21)$$

Solving this equation for $F_{max}$ and substituting into Equation (18) results in:

$$\theta_G = \bar{\theta}\frac{DDI}{\Psi} \qquad (22)$$

which can be used for $\theta_G$ in the main equation (Equation (17)).

Using an equivalent solution strategy for lateral flow, $\theta_L$ depends on a lateral flow index (LFI) according to:

$$\theta_L = \bar{\theta}\frac{LFI}{\Lambda} \qquad (23)$$

where:

$$LFI \equiv \phi\left(\frac{1-\lambda V}{\delta_0 t K_{s,v}}\right)^{1/\gamma_h}\left(\frac{A}{cS^\epsilon}\right)^{1/\gamma_h}\left(\frac{\kappa_{min}}{\kappa_{min}-\kappa}\right)^{1/\gamma_h} \qquad (24)$$

and $\Lambda$ is the spatial-average LFI. In some embodiments, to obtain these expressions, $F_{max}$ and $\gamma_h$ may be held constant. In some embodiments, the LFI is a compound topographic, vegetation, and soil index, which introduces another pattern of variation into the $\theta$ estimate. In some embodiments, $\theta_R$ can depend on a radiative ET index (REI) according to:

$$\theta_R = \bar{\theta}\frac{REI}{\Pi} \qquad (25)$$

where:

$$REI \equiv \phi\left(\frac{1-\alpha}{E_p}\right)^{1/\beta_r}\left(\frac{1}{I_p}\right)^{1/\beta_r}\left[\frac{1-\lambda V}{\eta V+(1-V)^\mu}\right]^{1/\beta_r} \qquad (26)$$

and $\Pi$ is the spatial-average REI. In some embodiments, to obtain these expressions, $F_{max}$ and/or $\beta_r$ may be held constant. In some embodiments, the REI can be a compound topographic, vegetation, soil, and climatic index.

In some embodiments, $\theta_A$ may depend on an aerodynamic ET index (AEI) according to:

$$\theta_A = \bar{\theta}\frac{AEI}{\Omega} \qquad (27)$$

where:

$$AEI \equiv \phi\left(\frac{1+\alpha}{E_p\alpha}\right)^{1/\beta_a}\left[\frac{1-\lambda V}{\eta V+(1-V)^\mu}\right]^{1/\beta_a} \qquad (28)$$

and $\Omega$ denotes the spatial-average AEI. In some embodiments, $F_{max}$ and/or $\beta_a$ may be held constant. In some embodiments, the AEI is a compound vegetation, soil, and climatic index that may introduce spatial variation into the $\theta$ estimate.

In some embodiments, the relative importance of $\theta_G$, $\theta_L$, $\theta_R$, and/or $\theta_A$ to the weighted average may be calculated from the magnitude of the associated term in Equation (16). For example, $w_G$ is equal to the deep drainage term in Equation (20) if $\theta_G$ is used in place of $\theta$. Any coefficients that appear in $w_G$, $w_L$, $w_R$, and/or $w_A$ may be cancelled because $w_G$, $w_L$, $w_R$, and/or $w_A$ appear in the numerator and denominator of Equation (17). For example, the coefficients can be represented as the following:

$$w_G = \left(\frac{\bar{\theta}}{\Psi}\right)^{\gamma_v} \qquad (29)$$

$$w_L = \left(\frac{\bar{\theta}}{\Lambda}\right)^{\gamma_h} \qquad (30)$$

$$w_R = \left(\frac{\bar{\theta}}{\Pi}\right)^{\beta_r} \qquad (31)$$

$$w_A = \left(\frac{\bar{\theta}}{\Omega}\right)^{\beta_a} \qquad (32)$$

In some embodiments, the fine-resolution variables may include one or more topographic attributes (A, S, $\kappa$, and/or $I_p$), vegetation characteristics (V, $\lambda$, $\eta$, and/or $\mu$), soil characteristics ($\phi$, t, $K_{s,v}$, $\delta_0$, $\kappa_{min}$, and/or $\epsilon$), and/or climate characteristics ($E_p$ and/or $\alpha$). Although spatial variability is allowed in these properties, the fine-resolution maps can use spatially constant values (or constant values within sub-regions). In some embodiments, an output may include a map of $\theta$ at the same fine-resolution as these inputs. Single constant values must be provided for $\gamma_v$, $\gamma_h$, $\beta_r$, $\beta_a$ and/or $\bar{\theta}$. These properties could also be specified on a coarse grid because each coarse grid cell may be downscaled independently. In some embodiments, all properties aside from $\bar{\theta}$ are treated as constant through time.

In some embodiments, various parameters and/or attributes may be considered coarse-resolution parameters and/or attributes such as, for example, $\bar{\theta}$, $\Psi$, $\Omega$, $\Pi$, and/or $\Lambda$. In some embodiments, $\bar{\theta}$, $\Psi$, $\Omega$, $\Pi$, and/or $\Lambda$ may represent an average value within a coarse-resolution grid cell. In some embodiments, $\bar{\theta}$, $\Psi$, $\Omega$, $\Pi$, and/or $\Lambda$ may represent an average window value calculated as the average of fine-resolution grid cells within a window centered on the fine resolution grid cell being calculated. $\bar{\theta}$, $\Psi$, $\Omega$, $\Pi$, and/or $\Lambda$ may represent an average value of adjacent fine-resolution grid cells.

In some embodiments, the parameters (or coefficients) $w_G$, $w_L$, $w_R$, and/or $w_A$ may be calculated from the following:

$$w_G = \left(\frac{\bar{\theta}}{\overline{DDI}}\right)^{\gamma_v}, \qquad (33)$$

$$w_L = \left(\frac{\bar{\theta}}{\overline{LFI}}\right)^{\gamma_h}, \qquad (34)$$

$$w_R = \left(\frac{\bar{\theta}}{\overline{REI}}\right)^{\beta_r}, \qquad (35)$$

$$w_A = \left(\frac{\bar{\theta}}{\overline{AEI}}\right)^{\beta_a} \qquad (36)$$

where $\overline{LFI}$ is the spatial average of LFI, $\overline{DDI}$ is the spatial average of the DDI, $\overline{REI}$ is the spatial average of the REI, and $\overline{AEI}$ is the spatial average of the AEI. In addition, the soil moisture estimates may be calculated from:

$$\theta_G = \bar{\theta}\frac{DDI}{\overline{DDI}} \qquad (37)$$

-continued $$\theta_L = \bar{\theta}\frac{LFI}{\overline{LFI}} \quad (38)$$

$$\theta_R = \bar{\theta}\frac{REI}{\overline{REI}} \quad (39)$$

$$\theta_A = \bar{\theta}\frac{AEI}{\overline{AEI}} \quad (40)$$

In some embodiments, the indices (DDI, LFI, REI, and/or AEI) may be calculated from the following:

$$DDI \equiv \qquad (41)$$
$$\phi\frac{[1+\tau(Z_\#-\bar{Z}_\#)]^{1/\gamma_v}\left\{\frac{1+\xi[S_\#\cos(R_\#-v)-]}{\overline{S_\#\cos(R_\#-v)]}}\right\}^{1/\gamma_v}}{\{1+\tau\xi[\overline{Z_\#S_\#\cos(R_\#-v)}-\bar{Z}_\#\overline{S_\#\cos(R_\#-v)]}\}^{1/\gamma_v}}\left(\frac{1-\lambda V}{K_{s,v}}\right)^{1/\gamma_v}$$

$$LFI \equiv \phi\frac{[1+\tau(Z_\#-\bar{Z}_\#)]^{1/\gamma_h}\left\{\frac{1+\xi[S_\#\cos(R_\#-v)-]}{\overline{S_\#\cos(R_\#-v)]}}\right\}^{1/\gamma_h}}{\{1+\tau\xi[\overline{Z_\#S_\#\cos(R_\#-v)}-\bar{Z}_\#\overline{S_\#\cos(R_\#-v)]}\}^{1/\gamma_h}} \quad (42)$$
$$\left(\frac{1-\lambda V}{\delta_0\iota K_{s,v}}\right)^{1/\gamma_h}\left(\frac{A}{cS^e}\right)^{1/\gamma_h}\left(\frac{\kappa_{min}}{\kappa_{min}-\kappa}\right)^{1/\gamma_h}$$

$$REI \equiv \phi\frac{[1+\tau(Z_\#-\bar{Z}_\#)]^{1/\beta_r}\left\{\frac{1+\xi[S_\#\cos(R_\#-v)-]}{\overline{S_\#\cos(R_\#-v)]}}\right\}^{1/\beta_r}}{\{1+\tau\xi[\overline{Z_\#S_\#\cos(R_\#-v)}-\bar{Z}_\#\overline{S_\#\cos(R_\#-v)]}\}^{1/\beta_r}} \quad (43)$$
$$\left\{\frac{1+\alpha}{\overline{E_p[1+\omega(\bar{Z}-Z)]}}\right\}^{1/\beta_r}\left(\frac{1}{I_p}\right)^{1/\beta_r}\left[\frac{(1-\lambda V)}{\eta V+(1-V)^\mu}\right]^{1/\beta_r}$$

$$AEI \equiv \phi\frac{[1+\tau(Z_\#-\bar{Z}_\#)]^{1/\beta_a}\left\{\frac{1+\xi[S_\#\cos(R_\#-v)-]}{\overline{S_\#\cos(R_\#-v)]}}\right\}^{1/\beta_a}}{\{1+\tau\xi[\overline{Z_\#S_\#\cos(R_\#-v)}-\bar{Z}_\#\overline{S_\#\cos(R_\#-v)]}\}^{1/\beta_a}} \quad (44)$$
$$\left\{\frac{1+\alpha}{\alpha\overline{E_p[1+\omega(\bar{Z}-Z)]}}\right\}^{1/\beta_a}\left[\frac{(1-\lambda V)}{\eta V+(1-V)^\mu}\right]^{1/\beta_a}$$

where Z represents topographic elevation; $\xi$ is a parameter that may control the orientation dependence; $v$ is a reference direction from which topographic orientations may be calculated; $\tau$ is a parameter that controls the elevation dependence; $Z_\#$, $S_\#$, and $R_\#$ are the average elevation, slope, and aspect, respectively, within a square neighborhood around the grid cell of interest; and $\bar{Z}$ is the average elevation in the region.

The performance of some results of some embodiments of the invention can be compared to that of the EOF downscaling method. These comparisons have been made on data from the Cache la Poudre, Tarrawarra, and Nerrigundah catchments and shall be discussed below.

The 8.0 ha Cache la Poudre catchment is located near Rustic, Colo. (40° 41' 56" N and 105° 30' 30" W). The climate is semi-arid with 415 mm mean annual precipitation.

The catchment has aspect-dependent vegetation with a coniferous forest with sparse deciduous shrub understory on the north-facing slope (NFS) and shrubland with sparse coniferous trees on the south-facing slope (SFS) (FIG. 2a). The NFS is dominated by *Ponderosa* Pine (*Pinus ponderosa*), while Douglas Fir (*Pseudotsuga menziesii*), Rocky Mountain Juniper (*Juniperous scopulorum*), and Common Juniper (*Juniperus communes*) are also present. The dominant understory shrubs are Mountain Mahogany (*Cercocarpus montanus*) and Antelope Bitterbrush (*Purshia tridentate*). The SFS consists primarily of Mountain Mahogany and Antelope Bitterbrush shrubs with Mountain Big Sagebrush (*Artemisia tridentate* subs. *vaseyana*) found at the lowest elevations. A few *Ponderosa* Pine and Rocky Mountain Juniper trees are also found on the SFS.

Figure 3A:
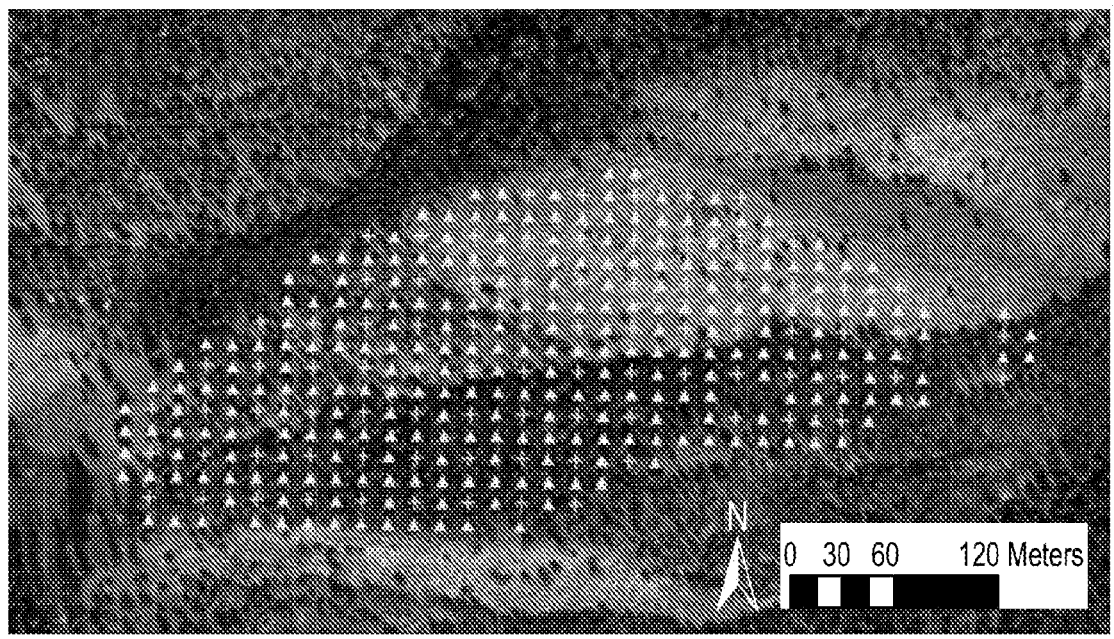
FIG. 3A illustrates 15 m and 30 m sampling grids overlaid on aerial photo of the Cache la Poudre catchment.
Figure 3B:
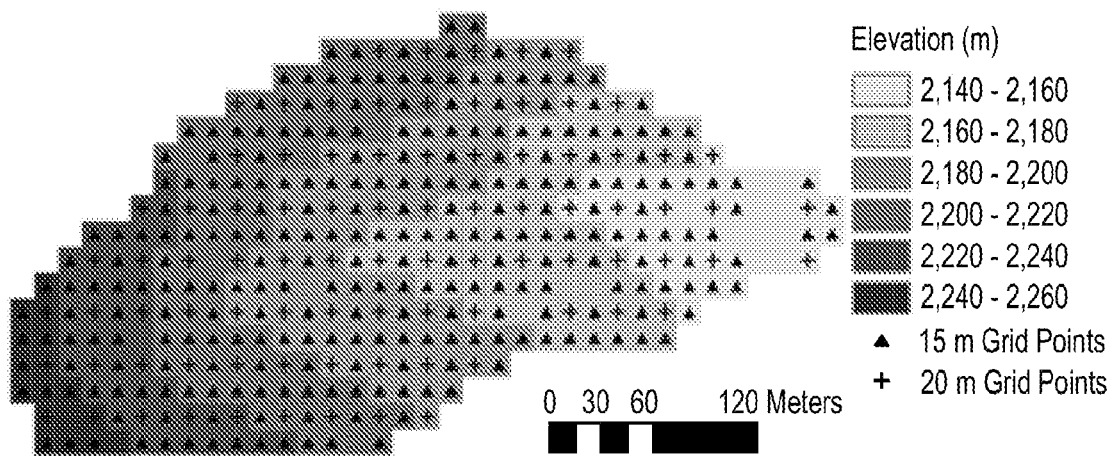
FIG. 3B illustrates sampling grids overlaid on catchment topography.

Soil moisture data were previously collected on a 15 m grid for the top 5 cm of the soil using time-domain reflectometry (TDR) (FIG. 3A). Measurements are available for nine dates between Apr. 22, 2008 and Jun. 24, 2008, and $\bar{\theta}$ ranges from 0.04 to 0.19. The sampling dates were selected to capture a sequence of soil moisture patterns as the catchment dries following rainfall events, and the monitoring period included two moderate rainfall events (2.9 cm and 4.7 cm). The range of soil moisture values in the dataset is typical for this catchment based on comparisons to longer records collected at fewer locations. Rather low soil moisture values occur in this catchment due to the relatively sandy and rocky soil composition. Only the 350 locations that were measured on all nine dates are used in this study. Elevation data were also previously surveyed on the same 15 m grid (FIG. 3B). The average elevation is approximately 2195 m and total relief is about 115 m.

Figure 4A:
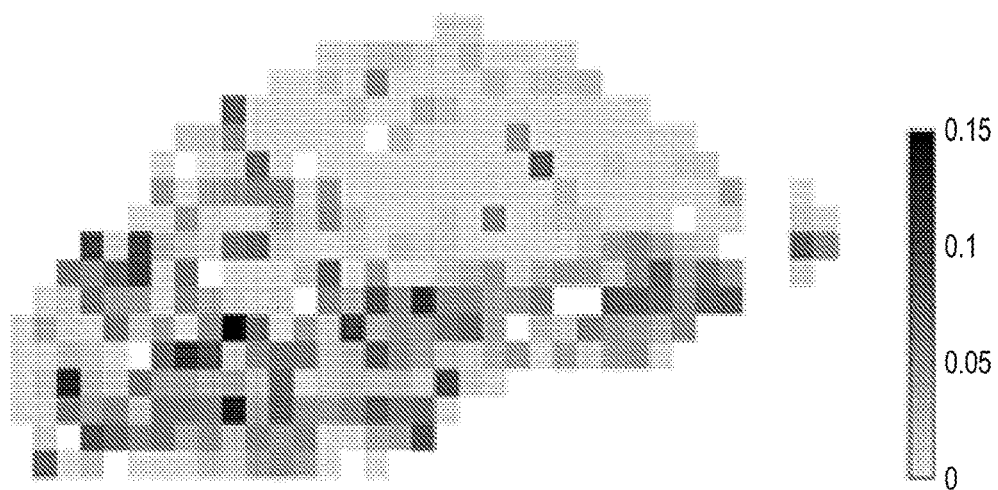
FIG. 4A illustrates vegetation data collected at the Cache la Poudre Catchment representing litter depth (m).
Figure 4B:
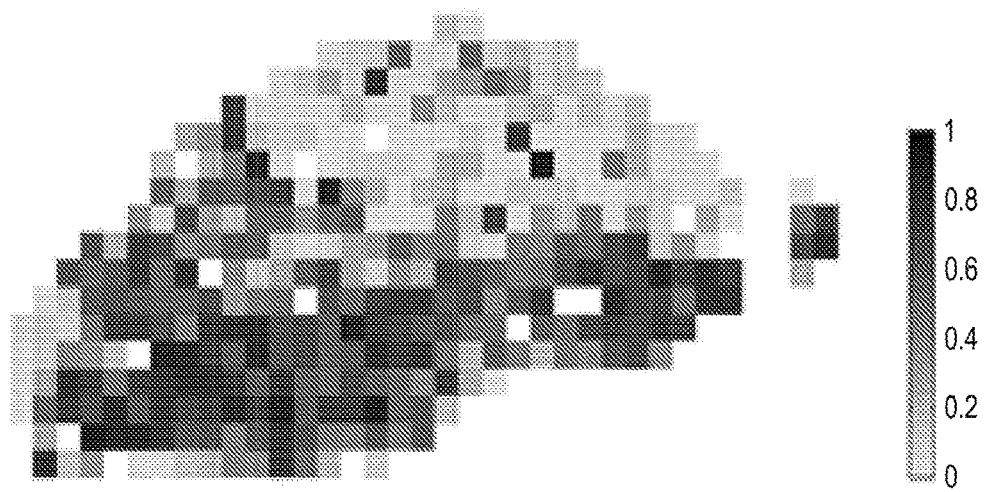
FIG. 4B illustrates vegetation data collected at the Cache la Poudre Catchment representing fractional canopy cover.

To characterize the vegetation cover, litter depth ($L_d$) and canopy cover ($C_c$) were measured on the 15 m grid in Fall 2008. Litter depth was measured manually, and the value for each grid point is the average of multiple measurements within 10 cm of the point (FIG. 4A). Litter depth ranges from 0 to 15 cm with an average of 3 cm. Canopy cover was determined from photographs that were taken vertically upward from the ground surface at each grid point. A 3.2 megapixel multispectral digital camera (e.g., a Tetracam Agriculture Digital Camera) was used, which has view angles of 31.6° and 39.4°. Images were analyzed using the PixelWrench software, which enables identification of canopy and sky pixels based on the red and infrared reflectance. The percent canopy coverage is calculated as a percentage of the pixels containing the partition assigned as vegetation. Unique parameter values were used to determine the partition in each image, but the partitioning can easily be confirmed by visual inspection of the images. The fraction of pixels that are vegetated was used for $C_c$ (FIG. 4B), which ranges from 0 to 0.90 with an average of 0.39. $C_c$ differs from the leaf area index (LAI) of the vegetation, because LAI accounts for multiple layers of vegetation cover and thus can have values above one. The patterns of both $L_d$ and $C_c$ strongly reflect the hillslope orientation. The correlations of $L_d$ and $C_c$ with the cosine of topographic aspect are 0.47 and 0.62, respectively.

The $L_d$ and $C_c$ measurements were combined to determine V. Both types of measurements are used because both canopy and litter cover can reduce soil evaporation and intercept rainfall. Although $L_d$ does not determine potential transpiration, both $C_c$ and $L_d$ are expected to be correlated with root density. Thus, both variables may be relevant, in this example, to V.

To determine V, $L_d$ is first transformed into fractional litter cover $L_c$ ($0 \leq L_c \leq 1$) as follows:

$$L_c = \tan h(L_d/\zeta) \quad (45)$$

where $\zeta$ is a calibrated reference litter depth ($\zeta > 0$). This transformation may be useful in some embodiments because litter depth is not bounded by zero and one. A hyperbolic tangent is used in the transformation, but other sigmoid functions may be used. The fractional vegetation cover is then calculated as follows:

$$V = L_c + C_c - L_c C_c \quad (46)$$

Figure 4C:
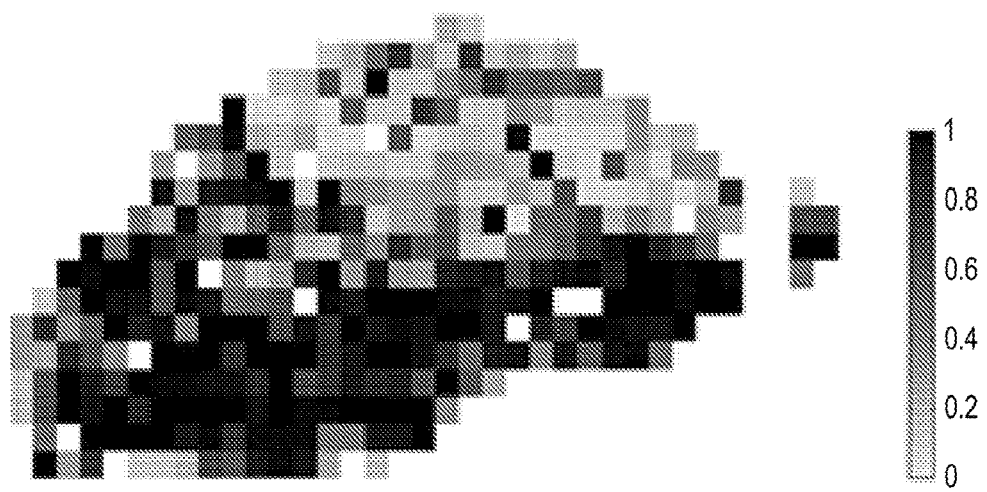
FIG. 4C illustrates vegetation data collected at the Cache la Poudre Catchment representing the calculated fractional vegetation cover.

The last term in this equation assumes that canopy cover and litter cover occur independently within a given fine-resolution grid cell. Because this assumption may not hold, V was also calculated by assuming a perfect correlation between these variables (in which case, V can be estimated from either $L_c$ or $C_c$ alone). All of these approaches tend to produce similar results because at the catchment-scale $L_d$ is well described by an exponential function of $C_c$. FIG. 4C shows V when it is calculated by Equation (46).

Soil samples (top 5 cm) were collected at alternating points from the 15 m grid (resulting in 86 points on a 30 m grid, FIG. 2). The fractions of coarse gravel (4.75-12.5 mm), fine gravel (2-4.75 mm), coarse sand (0.6-2 mm), and fine sand (0.05-0.6 mm) were determined by sieve analysis, and the fractions of silt (0.02-0.6 mm) and clay (<0.02 mm) were determined using the standard hydrometer method (see e.g., FIGS. 5A-C). Large spatial variations occur in the percent sand, silt, and clay, but little spatial organization is observed (FIG. 5). Silt is more abundant on the NFS and exhibits a correlation with cosine of aspect of 0.18.

Figure 5A:
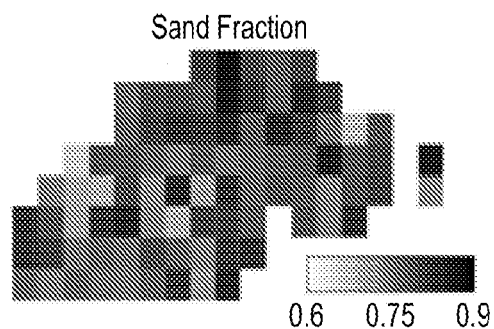
FIG. 5A illustrates the soil sample sand fraction.
Figure 5B:
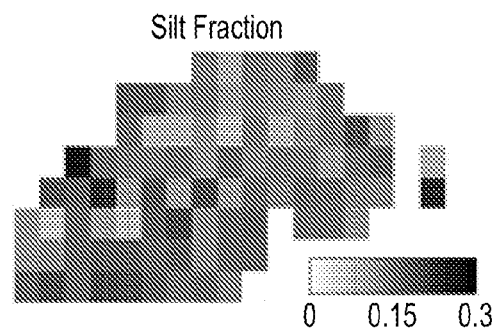
FIG. 5B illustrates the soil sample silt fraction.
Figure 5C:
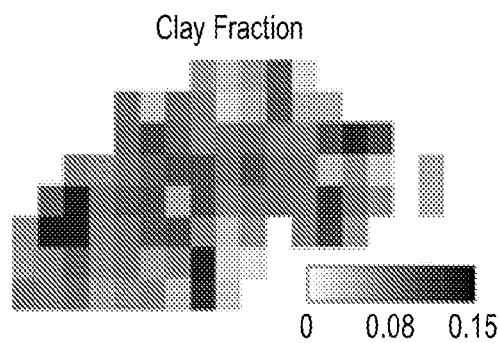
FIG. 5C illustrates the soil sample clay fraction.
Figure 5D:
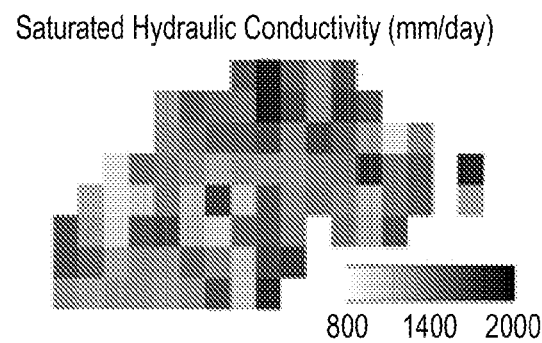
FIG. 5D illustrates the soil sample saturated hydraulic conductivity.
Figure 5E:
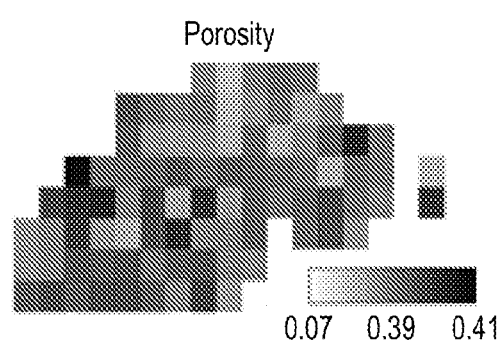
FIG. 5E illustrates the soil sample porosity.

Saturated hydraulic conductivity and $\phi$ were determined from the soil texture data using pedotransfer functions. Both functions were developed including A horizon samples, sandy loams, and topography with slopes up to 55%. Thus, they are expected to be appropriate for this catchment. However, the catchment includes an abundance of very large grain sizes, which might diverge from the datasets used to develop these functions. The resulting conductivity values range from 936 to 1845 mm/day with an average of 1356 mm/day and exhibit little spatial organization (see e.g., FIG. 5D). Because no information for anisotropy is available in this example, the conductivity values are used for $K_{s,v}$ and a spatially-constant anisotropy $\iota$ is calibrated to determine the horizontal saturated hydraulic conductivity. The $\phi$ values range from 0.38 to 0.41 (m³/m³) with an average of 0.39 (m³/m³) and also exhibits little spatial organization (FIG. 5E).

Figure 6A:
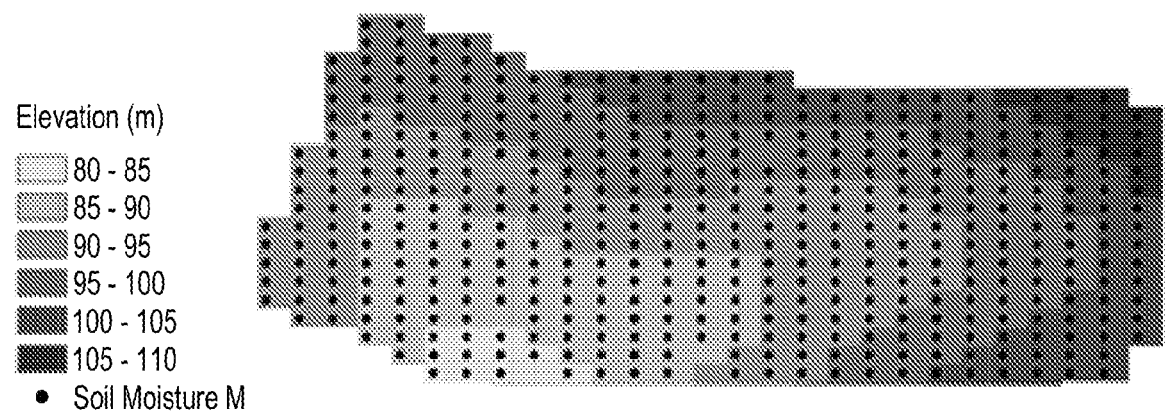
FIG. 6A illustrates soil moisture sampling grid at the Tarrawarra catchment overlaid on the catchment topography.

The 10.5 ha Tarrawarra catchment is located in southern Victoria, Australia. It has a temperate climate with mean annual precipitation of 820 mm. Soil moisture data are available on a 10 by 20 m grid for 13 dates from Sep. 27, 1995 to Nov. 29, 1996. The dates were selected to capture a typical range of moisture conditions during the year. The data were collected using a TDR in the top 30 cm of the soil. Only the 454 locations that are available on all 13 dates are used here. Topographic data are also available on a 5 m grid. The required topographical attributes (S, A, $\kappa$, and $I_p$) were determined using the 5 m DEM and then filtered to include only the cells with soil moisture measurements (see e.g., FIG. 6A).

Figure 6B:
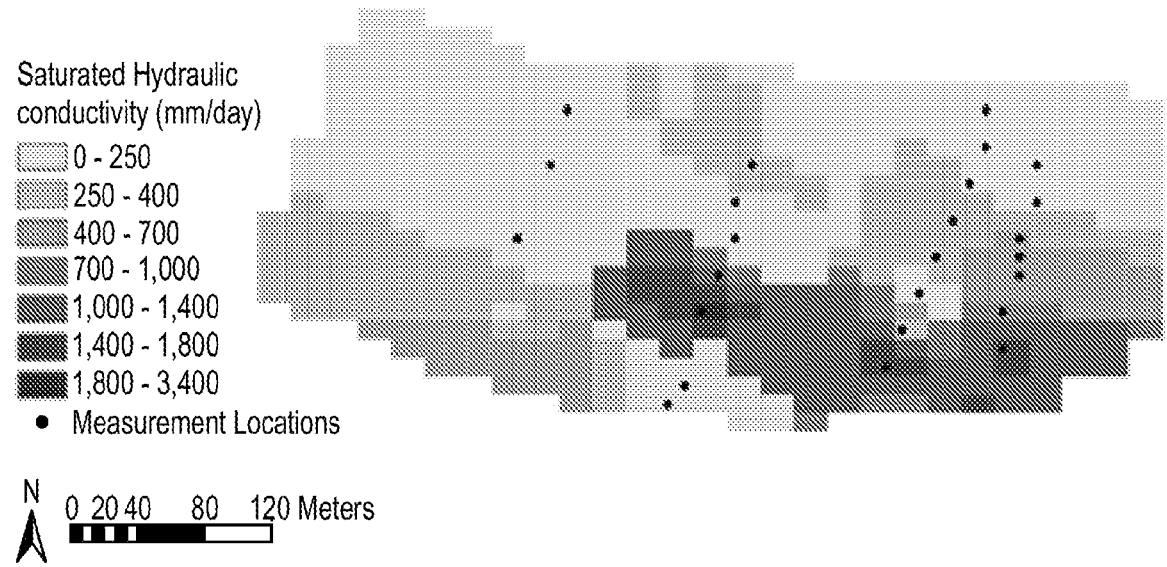
FIG. 6B illustrates saturated hydraulic conductivity measurement locations overlaid on the interpolated conductivity map.

Saturated hydraulic conductivity values are available from well permeameter tests at 42 locations. Some locations occur within the same soil moisture grid cells, in which case the observations were averaged to determine a single value for that cell. This procedure results in 32 cells with data. A complete hydraulic conductivity map was generated by interpolating between the observations with a linear inverse distance weighted (IDW) method using a search radius of 3 points. The resulting conductivity map exhibits higher values on the NFS (FIG. 6B). If similar variability occurs at Tarrawarra, then these interpolated conductivity values will contain significant errors. Similar to Cache la Poudre, anisotropy data are not available, so the conductivity values are used for $K_{s,v}$ and a is calibrated.

Some embodiments of the invention may use two variables ($\delta_0$ and $\kappa_{min}$) to determine the relationship between the thickness of the hydrologically active layer and topographic curvature $\kappa$. For Tarrawarra, the A horizon (e.g., 20 to 35 cm deep) is selected as the hydrologically active layer because the B horizon has low permeability compared to the A horizon. The A horizon thickness is available at 116 points on a 20 by 40 m grid. These observations were plotted against $\kappa$, and distinct relationships were observed where $\kappa$ is positive and negative. Thus, the catchment was divided into two soil groups based on the sign of the curvature and distinct values of $\delta_0$ and $\kappa_{min}$ were estimated from the data in those two groups.

Figure 7A:
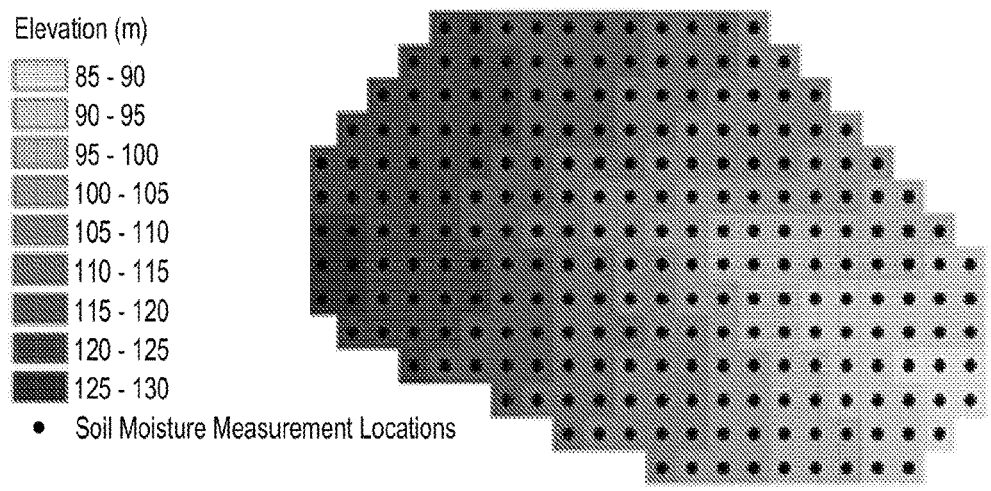
FIG. 7A illustrates an example soil moisture sampling grid at the Nerrigundah catchment overlaid on the catchment topography.

The 6.0 ha Nerrigundah catchment is located northwest of Dungog in New South Wales, Australia. It has temperate climate with an average annual precipitation of about 1000 mm. Soil moisture is available for the top 15 cm on a 20 m grid for 12 dates from Aug. 27, 1997 to Sep. 22, 1997. Only the 238 locations that are available on all 12 dates are used here. The soil moisture patterns from this catchment appear relatively similar perhaps because they were collected over a relatively short period. A 20 m DEM is also available and used to calculate the topographic attributes (e.g., FIG. 7A).

Figure 7B:
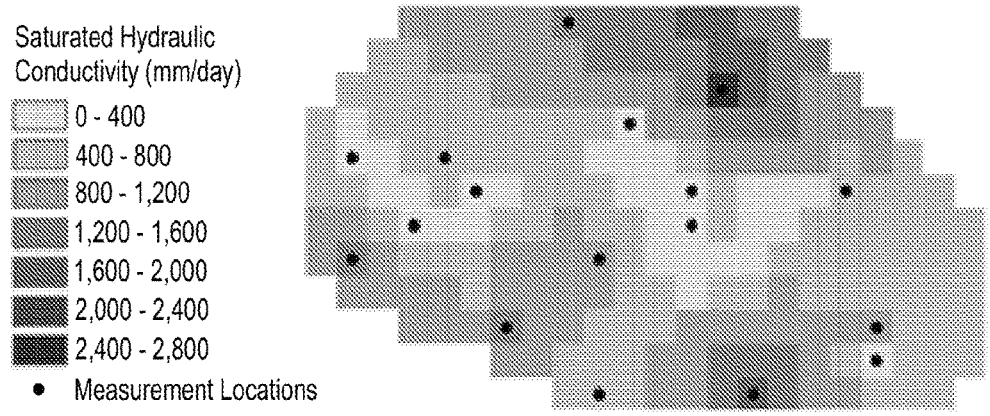
FIG. 7B illustrates saturated hydraulic conductivity measurement locations overlaid on the interpolated conductivity map.
Figure 7C:
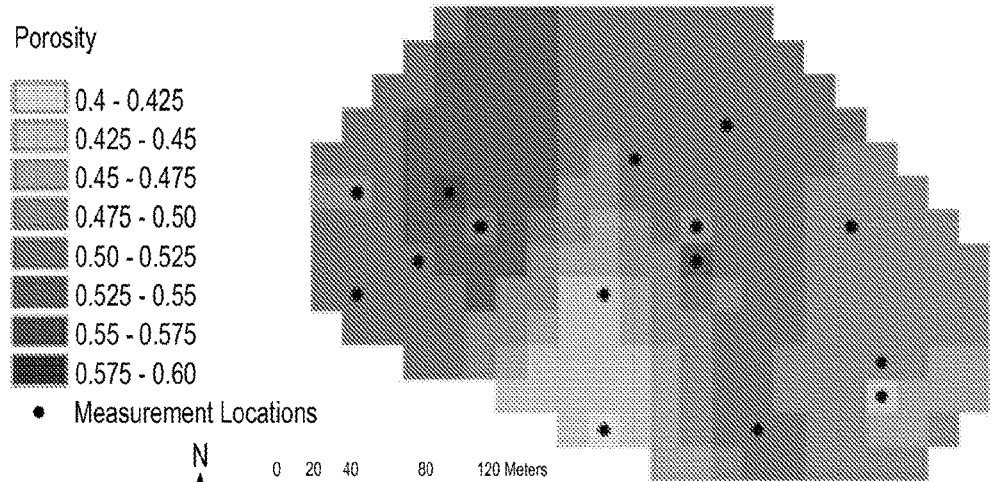
FIG. 7C illustrates porosity measurement locations overlaid on the interpolated porosity map.

Soil data are available at 19 locations. In particular, depths to the bottoms of the A1, A2, B1, and B2 horizons are available, and grain sizes, porosity, and saturated hydraulic conductivity values are available for all horizons. For Nerrigundah, the hydrologically active layer was assumed to extend to the bottom of the B1 horizon because the saturated hydraulic conductivity decreases substantially at this depth. The porosity for the hydrologically active layer was estimated from a weighted average of the porosities from the included horizons. Double-ring infiltrometer data were used to determine the conductivity values in the model because (among the available tests) they are most representative of the hydrologically active layer as a whole. Similar to Tarrawarra, when more than one conductivity or porosity value is available in a grid cell, those values were averaged, which results in 17 cells with conductivity data and 15 cells with porosity data. IDW interpolations were then used to generate values at all other locations. The interpolated conductivity map has higher values on the upper elevations of the NFS and SFS (FIG. 7B), while the porosity tends to be larger in the western portion of the catchment (FIG. 7C). Again, these interpolated maps might be unreliable, given the substantial local variations that were observed at Cache la Poudre. Similar to the other catchments, the conductivity data are used for $K_{s,v}$, and $\iota$ is calibrated.

In these examples, when a value was known from the available data for a catchment, it was used (e.g., $E_p$). Otherwise, the value was calibrated or estimated to maximize the average Nash Sutcliffe Coefficient of Efficiency (NSCE) for all dates in the catchment's soil moisture dataset (NSCE is equal to one minus the ratio of the squared error to the variance of the observations). If available, local information was used to determine the allowable range for the parameter (e.g., $\gamma_h$ and $\gamma_v$). Otherwise, broadly applicable ranges from other sources and/or theoretical bounds were used (e.g., $\lambda$, $\eta$, and $\mu$). The specified values and calibration ranges for all three test catchments are provided in Table 1.

To apply the EOF method, which is used as a comparison with the results from the EMT+VS model, the same topographic attributes used by Busch et al. (2012) are considered. These attributes include: slope (S), cosine of aspect, specific contributing area (A/c), the log of specific contributing area (ln(A/c)), the wetness index (ln [A/(cS)]), Laplace curvature, profile curvature, plan curvature, tangent curvature, and the PSRI ($I_p$). For Cache la Poudre, the litter depth ($L_d$) and canopy cover ($C_c$) data are supplied to the EOF method for scenarios when vegetation data are considered.

Similarly, percent sand, percent silt, percent clay, saturated hydraulic conductivity (used as $K_{s,v}$ in the EMT+VS model), and porosity ($\phi$) are supplied to the EOF method when soil properties are considered. For Tarrawarra, the fine-resolution $K_{s,v}$, $\delta_0$, and $\kappa_{min}$ values are supplied to the method when soil data are considered. For Nerrigundah, the fine-resolution conductivity (e.g., $K_{s,v}$) and porosity ($\phi$) values are supplied to the method when soil data are considered. In all cases, the EOF method is constructed using the soil moisture values from all dates in the available datasets.

Figure 8A:
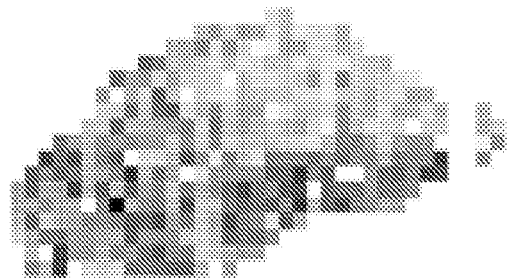
FIG. 8A illustrates the observed soil moisture pattern at Cache la Poudre on a date with intermediate moisture.
Figure 8B:
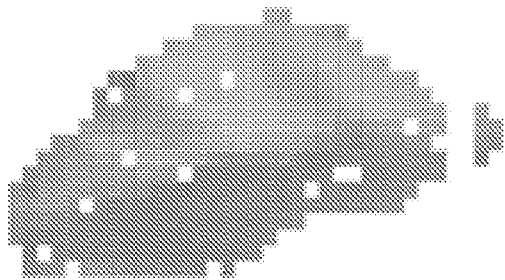
FIG. 8B illustrates an estimated soil moisture pattern at Cache la Poudre using the EOF model with fine-resolution topography information.
Figure 8C:
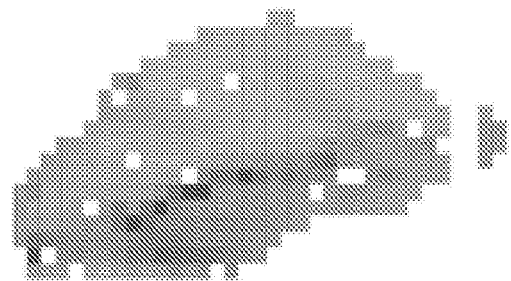
FIG. 8C illustrates an estimated soil moisture pattern at Cache la Poudre using a model according to some embodiments of the invention with fine-resolution topography information.
Figure 8D:
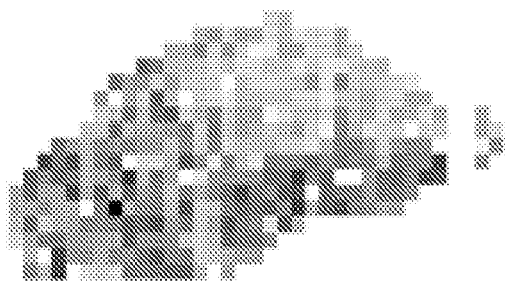
FIG. 8D illustrates an observed soil moisture pattern at Cache la Poudre with intermediate moisture.
Figure 8E:
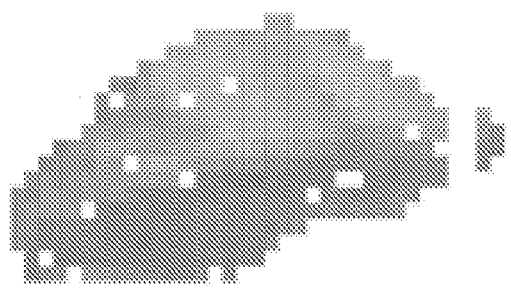
FIG. 8E illustrates an estimated soil moisture pattern at Cache la Poudre using the EOF model with fine-resolution topography and vegetation information.
Figure 8F:
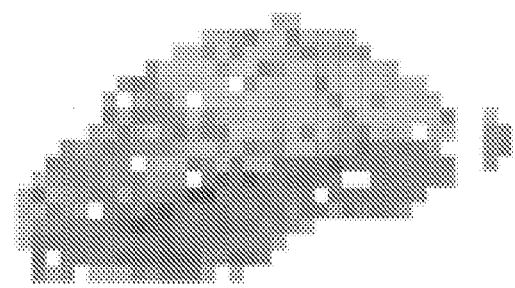
FIG. 8F illustrates an estimated soil moisture pattern at Cache la Poudre using a model according to some embodiments of the invention with fine-resolution topography and vegetation information.
Figure 8F:
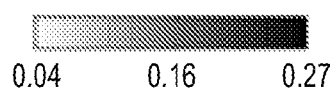

Table 1 shows upper and lower calibration ranges for model parameters and spatially-constant variables used at all three test catchments.

pattern from the EOF method (FIG. 8E) remains very similar although some additional local variability (speckle) is observed. However, $L_d$ and $C_c$ are now included in the estimation of the second EOF. In contrast, the soil moisture patterns from the (FIGS. 8C and 8F, respectively) are substantially different. The EMT+VS model, which include embodiments of the invention, may be more realistic because it captures the wetter conditions in the western part of the catchment and more of the local variability (particularly on the SFS).

The top half of Table 2 quantifies the performance of the downscaling methods for this scenario. The NSCE, root mean square error (RMSE), and mean relative error (MRE) were calculated for each date in the dataset, and the table

|  | | Poudre | | Tarrawarra | | Nerrigundah | |
|---|---|---|---|---|---|---|---|
|  | Parameter | Lower | Upper | Lower | Upper | Lower | Upper |
| Climate | $E_p$ (mm/day) | 2.4 | 2.4 | 2.3 | 2.3 | 2.8 | 2.8 |
|  | $\alpha$ | 0.26 | 0.26 | 0.26 | 0.26 | 0.26 | 0.26 |
| Vegetation | $\beta_r$ | 0.2 | 5 | 0.2 | 5 | 0.2 | 5 |
|  | $\beta_a$ | 0.2 | 5 | 0.2 | 5 | 0.2 | 5 |
|  | $\lambda$ | 0 | 1 | 0 | 1 | 0 | 1 |
|  | $\eta$ | 0 | 1 | 0 | 1 | 0 | 1 |
|  | $\mu$ | 1 | 3 | 1 | 3 | 1 | 3 |
|  | $\zeta$ (m) | 0.001 | N/A | N/A | N/A | N/A | N/A |
| Soil | $\phi$ (m$^3$/m$^3$) | 0.38 | 0.41 | 0.25 | 0.70 | 0.41 | 0.56 |
|  | $K_{s,v}$ (mm/day) | 936 | 1845 | 17 | 3355 | 36 | 2592 |
|  | $\iota$ | 1 | 100 | 1 | 100 | 1 | 100 |
|  | $\gamma_h$ | 1.0 | 13.0 | 1.0 | 25.0 | 1.0 | 17.3 |
|  | $\gamma_v$ | 9.2 | 13.0 | 4.0 | 25.0 | 10.9 | 17.3 |
|  | $\delta_0$ (m) | 0.05 | 0.05 | 0.23 | 0.23 | 0.25 | 0.25 |
|  | $\kappa_{min}$ (1/m) | −1E+06 | −0.0560 | −0.0267 | −0.0267 | −1E+06 | −0.0056 |
|  | $\epsilon$ | 1 | 3 | 1 | 3 | 1 | 3 |

In some embodiments, 15 m resolution data is supplied with fine-resolution topographic and vegetation data. In this example, the soil data are not used, so $K_{s,v}$ is calibrated (a second scenario that includes the soil data is discussed later). FIG. 8 shows the results for a date with a typical observed soil moisture pattern. The observed pattern (FIG. 8A) exhibits wetter conditions on the NFS than the SFS, and the western part of the catchment is wetter than the eastern part. Substantial local variations in soil moisture are also observed. When only topographic data are used, the downscaled pattern from the EOF method (FIG. 8B) is more realistic than the pattern from the EMT+VS model (FIG. 8C) because it better represents the wetter conditions in the western part of the catchment. For this dataset, the EOF method identifies two significant EOFs that explain 50% and 14% of the variance. The first EOF depends only on $I_p$, while the second EOF depends on $I_p$ and plan curvature. When both topographic and vegetation data are included, the provides the average values for each metric. Overall, estimates using both vegetation and topographic data perform better than just using topographic data, which suggests that vegetation plays a significant role in determining the soil moisture patterns and that embodiments of the invention captures some of that role. Estimates produced using embodiments of the invention also perform slightly better than the EOF method when vegetation data are included, which suggests that the representation of vegetation using embodiments of the invention is better than the linear dependence assumed in the EOF method.

Table 2 shows measures of model performance when the downscaling models are supplied with various fine-resolution datasets and applied to Cache la Poudre. The NSCE, root mean square error (RMSE), and mean relative error (MRE) are calculated separately for each date in the dataset and then the averages, maximums, and minimums are determined from the different dates.

|  |  |  | NSCE | | | RMSE | MRE |
|---|---|---|---|---|---|---|---|
| Grid | Scenario | Model | Avg. | Max. | Min. | Avg. | Avg. |
| 15 m | Topography | EMT | 0.080 | 0.183 | −0.027 | 0.031 | 0.453 |
|  |  | EOF | 0.116 | 0.288 | −0.050 | 0.030 | 0.438 |
|  | Topography and Vegetation | EMT + VS | 0.134 | 0.375 | −0.099 | 0.030 | 0.430 |
|  |  | EOF | 0.129 | 0.320 | −0.070 | 0.030 | 0.434 |
| 30 m | Topography | EMT | 0.099 | 0.227 | 0.015 | 0.030 | 0.485 |
|  |  | EOF | 0.172 | 0.399 | −0.030 | 0.029 | 0.448 |

-continued

| Grid | Scenario | Model | NSCE Avg. | NSCE Max. | NSCE Min. | RMSE Avg. | MRE Avg. |
|---|---|---|---|---|---|---|---|
| | Topography and Vegetation | EMT + VS | 0.187 | 0.498 | −0.089 | 0.029 | 0.463 |
| | | EOF | 0.190 | 0.405 | 0.008 | 0.028 | 0.453 |
| | Topography, Veg., and Soil | EMT + VS | 0.196 | 0.495 | −0.080 | 0.028 | 0.457 |
| | | EOF | 0.226 | 0.391 | 0.050 | 0.027 | 0.437 |

Table 2 characterizes the ability of the EMT+VS model to reproduce the soil moisture datasets that are used for calibration. The model can also be evaluated by calibrating with a subset of the data and then judging the performance on the data that were withheld. In these tests, eight dates were used to calibrate the EMT+VS model, and the performance was judged on the ninth date. This procedure was repeated until each date was withheld from the calibration, and then average NSCE values were calculated from all repetitions. The average NSCE for the eight dates that were used for calibration is 0.136, the average NSCE for the withheld dates is 0.115, and the average NSCE for the entire dataset when calibrated in this fashion is 0.133.

NSCE can also be calculated by considering the entire space-time soil moisture dataset at once. When calculated in this manner, the NSCE includes the spatial and temporal variation that is reproduced by the downscaling method. The space-time NSCE is 0.788 for the EMT+VS model when all dates are included in the calibration. The method is effective at capturing temporal variability because the measured B is provided as an input and the observed temporal variance of soil moisture is relatively large. Thus, knowledge of on each date provides considerable information about the soil moisture value at any given location within the catchment. Nonetheless, the high value indicates that estimates from the EMT+VS model are accurate enough to be useful.

Figure 9:
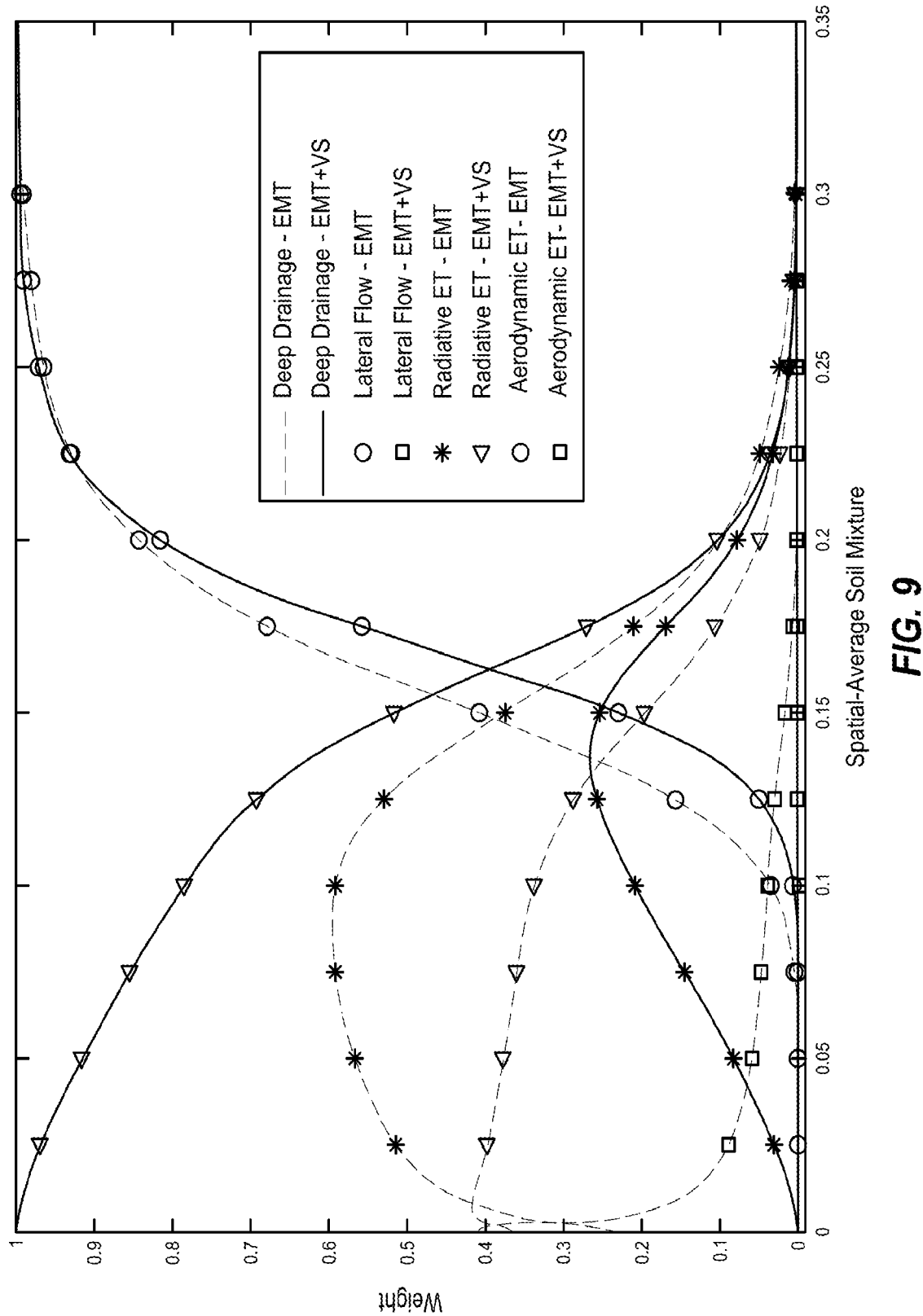
FIG. 9 illustrates calibrated weights for Cache la Poudre as a function of spatial-average soil moisture.

The weights that are used to estimate θ in the various models for this example are shown in FIG. 9. These examples of embodiments of the invention suggest that lateral flow plays little role in determining the soil moisture patterns in the dataset. When only topographic data are used, the model exhibits an increase in the lateral flow weight for very low $\bar{\theta}$ values, which is unexpected because lateral flow is generally considered to be more important under wetter conditions. In contrast, the lateral flow weight when topography and vegetation are used is always zero. The model with vegetation data may also have smaller values of the radiative ET weight and larger values of the aerodynamic ET weight than the model without vegetation. The reduction in the radiative ET weight may suggest that some of the soil moisture variation that was attributed to variations of insolation (i.e., radiative ET) in the model without vegetation data may be explained by variations in vegetation cover, which affect both the radiative and aerodynamic ET in the EMT+VS model. Because the vegetation cover is highly dependent on hillslope orientation, vegetation variations could easily be misattributed as insolation variations in a model that only considers topography.

FIG. 9 illustrates calibrated weights for the Cache la Poudre catchment as a function of spatial-average soil moisture with dashed lines representing the model without vegetation and solid lines representing the model with vegetation. The x-axis is positioned slightly below zero to better show weights that are zero. Symbols are shown (at a regular spacing) to distinguish the curves.

Figure 10A:
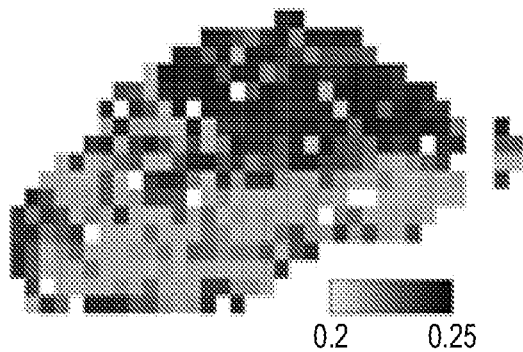
FIG. 10A illustrates the effect of the deep drainage index on the soil moisture estimate using some embodiments of the invention.

The patterns of variation that may be used to estimate the soil moisture in the model according to some embodiments are shown in FIGS. 10A, 10B, 10C, and 10D. FIG. 10A illustrates the effect of DDI on the soil moisture estimate. The DDI, for example, may depend on vegetation cover because of vegetation's role in interception. In some embodiments, the DDI may have larger values on the SFS where the sparse vegetation reduces interception. Thus, for wet conditions when deep drainage dominates, the model with vegetation data would produce patterns that are wetter on the SFS than NFS, while the model without vegetation would produce uniform soil moisture.

Figure 10B:
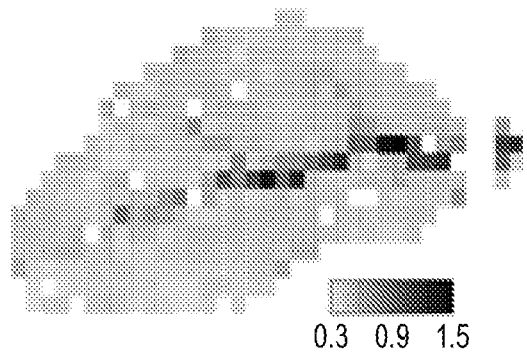
FIG. 10B illustrates the effect of lateral flow index on the soil moisture estimate using some embodiments of the invention.

FIG. 10B illustrates the effect of LFI on the soil moisture estimate.

Figure 10C:
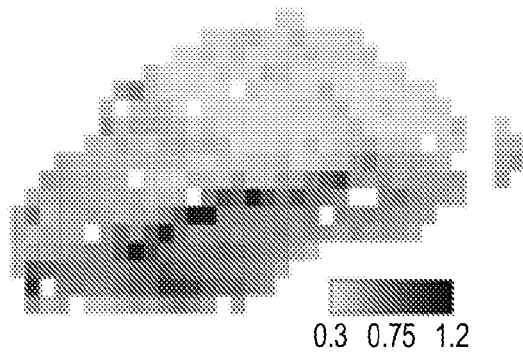
FIG. 10C illustrates the effect of radiative evapotranspiration index on the soil moisture estimate using some embodiments of the invention.

FIG. 10C illustrates the effect of REI on the soil moisture estimate. In some embodiments, the REI pattern in the model with vegetation data may be analogous to the ETI pattern in the model without vegetation. In this example, both patterns may have higher values on the NFS because that slope receives less insolation. However, the REI may also incorporate vegetation, which introduces more local variability in the REI pattern than the ETI pattern.

Figure 10D:
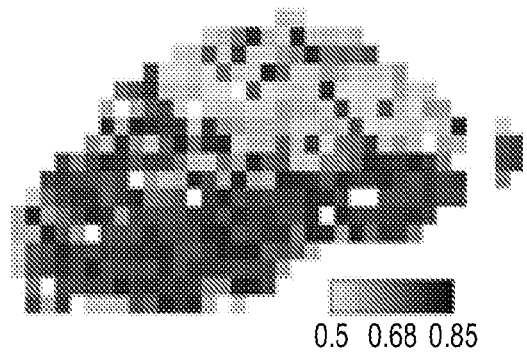
FIG. 10D illustrates the effect of aerodynamic evapotranspiration index on the soil moisture estimate using some embodiments of the invention.

FIG. 10D illustrates the effect of AEI on the soil moisture estimate. In some embodiments, the AEI may depend only on the vegetation cover. It has larger values on the NFS and the western portion of the catchment where the vegetation cover is thicker, and it promotes greater soil moisture in those areas.

Additional tests were run to determine the particular roles of vegetation that are important to the results from some embodiments of the invention. In some embodiments, interception may be neglected by setting λ=0 and recalibrating the other parameters. The average NSCE for this test is nearly identical to the original application of the EMT+VS model, which indicates that interception is not critical to the model performance for this dataset. Interception likely plays a small role because the dataset primarily considers dry conditions.

As another example, root-water uptake may be neglected. The average NSCE for this test may be lower than the original model application, which suggests that including root-water uptake may be valuable in some cases. In this example, however, the calibrated η value is only 0.06, so only a small fraction of the transpiration is derived from the hydrologically active layer. This low value is also expected because the layer is restricted to the top 5 cm, but the vegetation is primarily shrubs and trees, which have much greater rooting depths than 5 cm.

Figure 11:
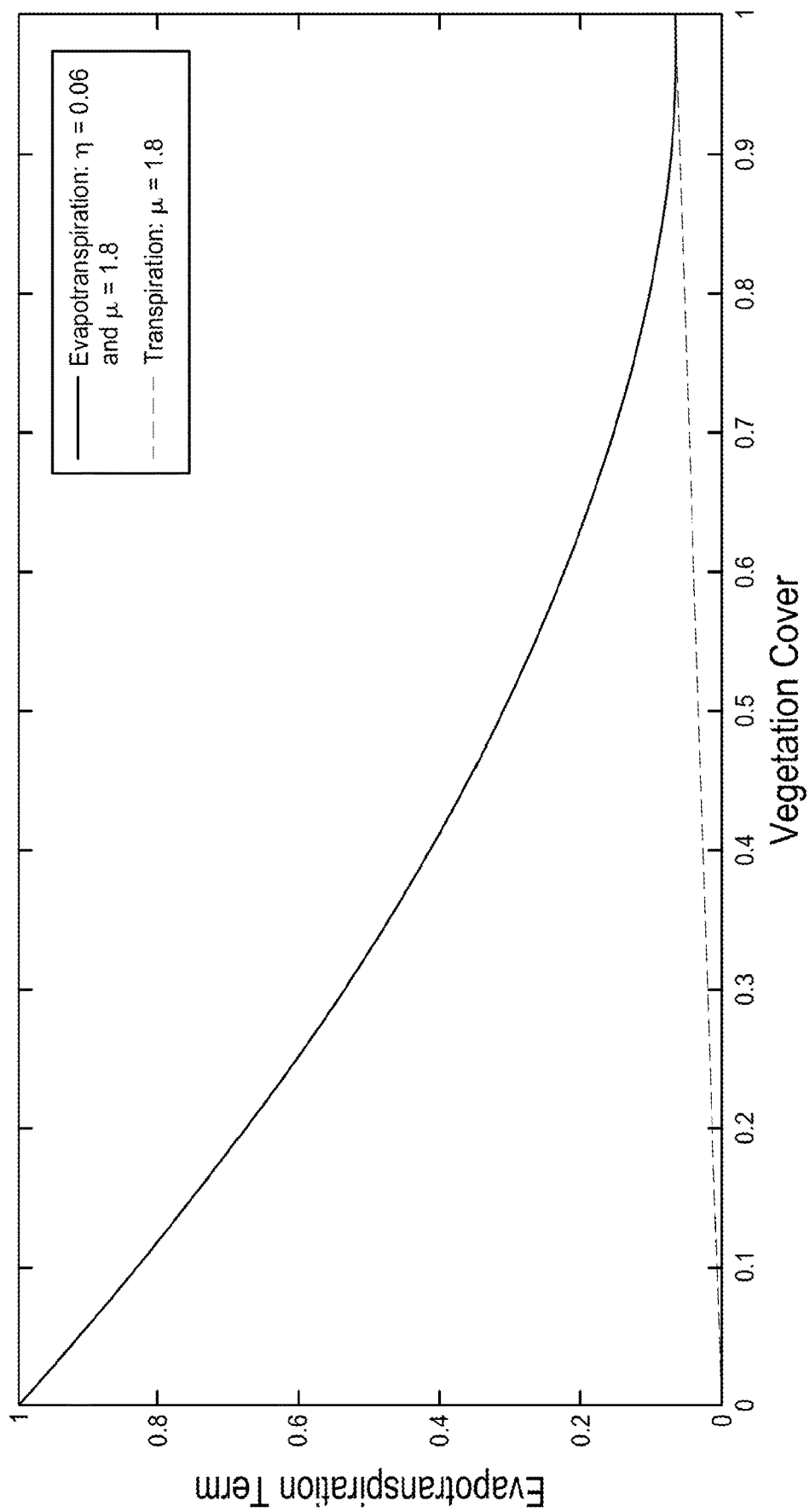
FIG. 11 is a graph illustrating overall effect of vegetation on evapotranspiration according to some embodiments.

As yet another example, the role that vegetation plays in reducing soil evaporation beyond redirecting available energy to transpiration may be neglected by setting μ=1 and recalibrating all other parameters. The average NSCE for this test may be nearly the same as the original application of the EMT+VS model. Thus, the compounded reduction in soil evaporation may not be critical to the model performance. The overall effect of vegetation is shown in FIG. 11, which uses the calibrated parameter values from the model according to some embodiments of the invention. ET from the hydrologically active layer substantially decreases as vegetation cover increases because the canopy reduces soil evaporation to increase total transpiration, yet transpiration from the modeled soil layer is very small.

FIG. 11 is a graph illustrating overall effect of vegetation on evapotranspiration according to some embodiments. In this graph, the ET term is plotted as a function of vegetation cover V when the associated parameters are calibrated to the Cache la Poudre dataset at a 15 m resolution. The dotted line shows the contribution of the transpiration term to the total ET term, and the space between the two lines shows the contribution of the evaporation term.

The EMT+VS model's use of fine-resolution soil data can be evaluated. For this evaluation, the EMT+VS model is applied at a 30 m resolution and supplied with fine-resolution topographic, vegetation, and soil ($K_{s,v}$ and $\phi$) data. This case is compared to the EMT+VS model when only topographic and vegetation data are used and the EOF method when it is supplied with comparable datasets. Considering a relatively wet date ($\bar{\theta}$=0.15) as an example, the results of the EOF method change somewhat when the soil data are supplied (e.g., comparing FIGS. 12B and 12D), but the main features of the patterns are the same. The EOF method uses the supplied percent silt data to improve the estimate of the first EOF, but the $K_{s,v}$ and $\phi$ data are not selected in the linear regressions that are used to estimate the EOFs. The results of the EMT+VS model may also change somewhat when soil data are provided (comparing FIGS. 12C and 12E), but the variations in vegetation continue to control the EMT+VS soil moisture patterns. $K_{s,v}$ may only affect the DDI and LFI, so this dataset plays a small role at this catchment (recall that the LFI has no role and the DDI is only important for wet dates). In contrast, $\phi$ appears in all four indices, so locations with higher $\phi$ values tend to be a little wetter (FIG. 12E). All patterns in FIGS. 12A-12F are on a 30 m grid, and units are m³/m³.

The bottom half of Table 2 provides the average performance of the models for the 30 m scenario. Including the fine-resolution vegetation data in the model improves its average performance (similar to what was observed for the 15 m scenario). Including the soil data as well produces only a small additional improvement (the average NSCE for the EMT+VS model increases only 0.009). Most of the improvement is due to $\phi$ because only two dates in the dataset are wet enough to have substantial deep drainage. The average performance of the EMT+VS model when soil data are included is below that of the EOF method when it uses comparable data. Nonetheless, when the soil data are included in the EMT+VS model, the space-time NSCE increases to 0.807, which again indicates good overall performance.

At Tarrawarra, the EMT+VS model's use of fine-resolution data for $K_{s,v}$, $\delta_0$, and $\kappa_{min}$ have been evaluated. Because vegetation data are not available and vegetation is a dense perennial grass, V=1 is assumed for all locations in the catchment. Considering a date with intermediate moisture as an example, the observed soil moisture pattern (FIG. 13A) has valley bottoms that are wetter than the hillslopes. In addition, the NFS is drier than the SFS. When only fine-resolution topographic data are used in the EOF method (FIG. 13B), the downscaled pattern reproduces these features. For this scenario, the EOF method identifies three significant EOFs that explain 55%, 9%, and 6% of the variance. The first and third EOFs depend on multiple topographic attributes but most strongly on the wetness index. The second EOF depends most strongly on $I_p$. The EMT model also produces similar tendencies (FIG. 13C), but its soil moisture pattern has a smaller difference in the soil moisture of the opposing hillslopes than the observed pattern.

When the soil data are added to the EOF method (FIG. 13D), the downscaled pattern appears almost unchanged. The EOF method uses the $K_{s,v}$ data to improve the estimates of the first and third EOFs, but they have very little effect on the results. The EOF method does not select the $\delta_0$ or $\kappa_{min}$ data in the regressions. When the soil data are included in the model with vegetation data, the results differ noticeably from the model without vegetation data (FIGS. 13C and 13E). In particular, the NFS is now drier than the SFS (similar to the observed pattern), but the configuration of the dry region on the NFS does not match the observations well. Locations with larger $K_{s,v}$ values are drier in the downscaled pattern because the LFI and DDI are both important for this date (see $K_{s,v}$ pattern in FIG. 6B), so this mismatch might occur because the $K_{s,v}$ data were interpolated from relatively sparse locations. The $\delta_0$ and $\kappa_{min}$ datasets have relatively little impact on the soil moisture pattern from the EMT+VS model.

Table 3 quantifies the average performance of the downscaling methods for Tarrawarra. The EOF method has similar performance irrespective of whether the soil data are provided. This similarity implies that the soil data are not very useful for estimating the EOFs, and thus it might suggest that the interpolated maps are unreliable. When the soil data are included in the EMT+VS model, the average performance deteriorates. While the EOF method uses only attributes that are correlated with the EOFs, the EMT+VS model may use the supplied data instead of calibrated constant values.

Table 3 shows measures of model performance when the downscaling models are supplied with various fine-resolution datasets and applied to Tarrawarra. The NSCE, RMSE, and MRE are calculated separately for each date in the dataset and then the averages, maximums, and minimums are determined from the different dates.

| Scenario | Model | NSCE | | | RMSE | MRE |
| --- | --- | --- | --- | --- | --- | --- |
| | | Avg. | Max. | Min. | Avg. | Avg. |
| Topography | EMT | 0.290 | 0.562 | 0.045 | 0.028 | 0.064 |
| | EOF | 0.350 | 0.655 | 0.068 | 0.027 | 0.061 |
| Topography and Soil | EMT + VS | 0.258 | 0.555 | −0.027 | 0.029 | 0.066 |
| | EOF | 0.356 | 0.662 | 0.077 | 0.027 | 0.061 |

Figure 14A:
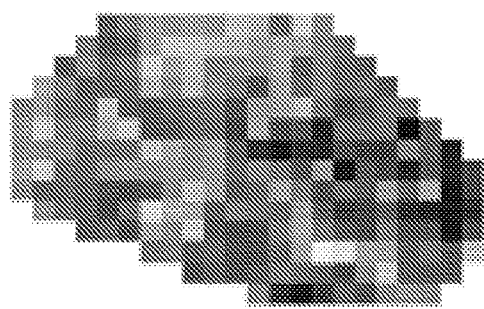
FIG. 14A illustrates the observed soil moisture pattern at Nerrigundah with intermediate moisture.
Figure 14B:
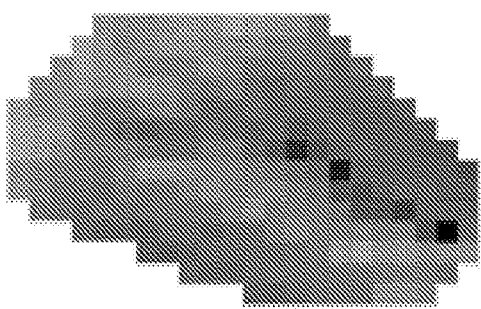
FIG. 14B illustrates an estimated soil moisture pattern at Nerrigundah using the EOF model with fine-resolution topography information.
Figure 14C:
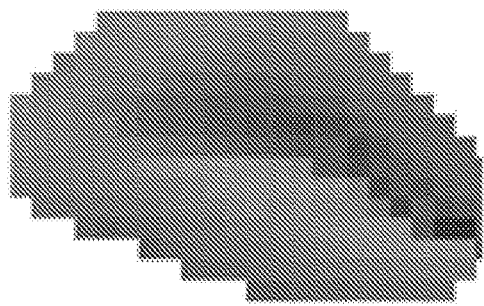
FIG. 14C illustrates an estimated soil moisture pattern at Nerrigundah using the EMT+VS model with fine-resolution topography information.
Figure 14D:
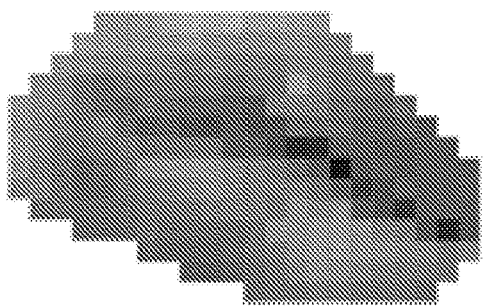
FIG. 14D illustrates an estimated soil moisture pattern at Nerrigundah using the EOF model with fine-resolution topography and soil (hydraulic conductivity) information.

The EMT+VS model's use of fine-resolution $K_{s,v}$ and $\phi$ data at Nerrigundah can be evaluated. Because vegetation data are not available and vegetation is natural grass, V=1 can be assumed for all locations in the catchment. The model is first applied when only the fine-resolution $K_{s,v}$ data are included ($\phi$ is calibrated). For an example date with intermediate moisture (FIG. 14A), the observed soil moisture pattern exhibits wetter conditions on the SFS than the NFS in the eastern half of the catchment. The western half of the catchment is generally drier and exhibits little dependence on hillslope orientation. When only topographic data are used in the EOF method (FIG. 14B) and the EMT+VS model (FIG. 14C), the downscaled patterns also exhibit the wetter conditions for the SFS than the NFS. However, the difference between the eastern and western halves of the catchment is not well reproduced. The EOF method identifies only one significant EOF that explains 75% of the variance. This EOF depends to some extent on most of the supplied topographic attributes. When the $K_{s,v}$ data are added to the EOF method (FIG. 14D) and the EMT+VS Model according to some embodiments (FIG. 14E), the downscaled patterns exhibit more distinct dry regions on the NFS, which correspond to areas of higher $K_{s,v}$ (e.g., FIG. 7B). The EMT+VS pattern is determined primarily by the REI and DDI. Because the DDI depends on $K_{s,v}$, the downscaled pattern reflects the $K_{s,v}$ pattern to a certain extent. The average performance from all dates (Table 4) indicates the EOF method performance improves when the $K_{s,v}$ data are provided, which indicates that the $K_{s,v}$ data can be beneficial. Similarly, the EMT+VS model outperforms the EMT model, but its performance remains below the EOF method when comparable data are used.

Figure 14E:
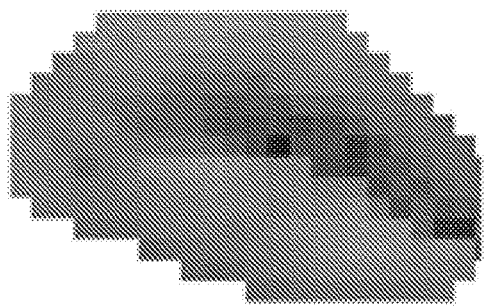
FIG. 14E illustrates an estimated soil moisture pattern at Nerrigundah using the EMT+VS model with fine-resolution topography and soil (hydraulic conductivity) information.
Figure 14F:
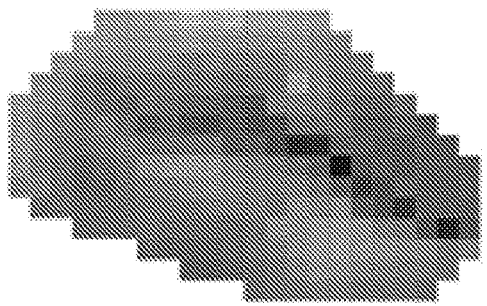
FIG. 14F illustrates an estimated soil moisture pattern at Nerrigundah using the EOF model with fine-resolution topography and soil information (hydraulic conductivity and porosity).
Figure 14G:
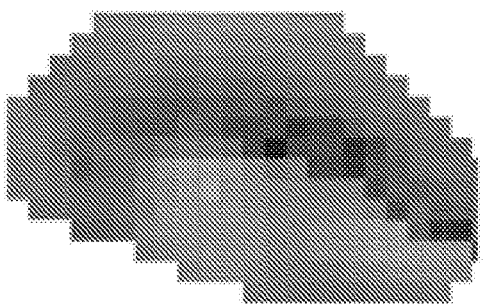
FIG. 14G illustrates an estimated soil moisture pattern at Nerrigundah using the EMT+VS model with fine-resolution topography and soil information (hydraulic conductivity and porosity).

Next, the EOF method and the EMT+VS model are supplied with both the fine-resolution $K_{s,v}$ and $\phi$ datasets. For the example date, the EOF method produces an identical pattern (FIG. 14F) to the previous case (FIG. 14D) because the $\phi$ data are not selected in the regressions. Again, this behavior might occur because the $\phi$ patterns are unreliable. However, when the $\phi$ data are added to the EMT+VS model (FIG. 14G), the downscaled pattern differs from the previous case (FIG. 14E). The EMT+VS model must use the $\phi$ data in all four indices. As a result, more distinct dry regions now occur. Although the observed pattern has similar dry regions, they do not exactly align with the dry areas in the downscaled pattern. It is possible that the EMT+VS model is capturing some soil moisture variations that are due to $\phi$ variations, but that the interpolated $\phi$ map does not correctly identify the configuration of those variations.

Table 4 shows measures of model performance when the downscaling models are supplied with various fine-resolution datasets and applied to Nerrigundah. The NSCE, RMSE, and MRE are calculated separately for each date in the dataset and then the averages, maximums, and minimums are determined from the different dates.

| Scenario | Model | NSCE Avg. | NSCE Max. | NSCE Min. | RMSE Avg. | MRE Avg. |
|---|---|---|---|---|---|---|
| Topography | EMT | 0.182 | 0.222 | 0.143 | 0.048 | 0.165 |
| | EOF | 0.274 | 0.326 | 0.087 | 0.045 | 0.155 |
| Topography and Soil ($K_{s,v}$) | EMT + VS | 0.218 | 0.281 | 0.088 | 0.047 | 0.161 |
| | EOF | 0.291 | 0.348 | 0.178 | 0.045 | 0.151 |
| Topography and Soil ($K_{s,v}$ and $\phi$) | EMT + VS | 0.115 | 0.282 | −0.022 | 0.050 | 0.170 |
| | EOF | 0.291 | 0.348 | 0.178 | 0.045 | 0.151 |

The various flowcharts, processes, computers, servers, etc. described in this document may be executed, for example, using the computational system 1500 (or processing unit) illustrated in FIG. 15. For example, the computational system 1500 can be used alone or in conjunction with other components. As another example, the computational system 1500 can be used to perform any calculation, solve any equation, perform any identification, and/or make any determination described herein.

The computational system 1500 may include any or all of the hardware elements shown in the figure and described herein. The computational system 1500 may include hardware elements that can be electrically coupled via a bus 1505 (or may otherwise be in communication, as appropriate). The hardware elements can include one or more processors 1510, including, without limitation, one or more general-purpose processors and/or one or more special-purpose processors (such as digital signal processing chips, graphics acceleration chips, and/or the like); one or more input devices 1515, which can include, without limitation, a mouse, a keyboard, and/or the like; and one or more output devices 1520, which can include, without limitation, a display device, a printer, and/or the like.

The computational system 1500 may further include (and/or be in communication with) one or more storage devices 1525, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational system 1500 might also include a communications subsystem 1530, which can include, without limitation, a modem, a network card (wireless or wired), an infrared communication device, a wireless communication device, and/or chipset (such as a Bluetooth® device, a 802.6 device, a Wi-Fi device, a WiMAX device, cellular communication facilities, etc.), and/or the like. The communications subsystem 1530 may permit data to be exchanged with a network (such as the network described below, to name one example) and/or any other devices described herein. In many embodiments, the computational system 1500 will further include a working memory 1535, which can include a RAM or ROM device, as described above.

The computational system 1500 also can include software elements, shown as being currently located within the working memory 1535, including an operating system 1540 and/or other code, such as one or more application programs 1545, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1525 described above.

In some cases, the storage medium might be incorporated within the computational system 1500 or in communication with the computational system 1500. In other embodiments, the storage medium might be separate from the computational system 1500 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 1500 and/or might take the form of source and/or installable code, which, upon compilation and/or installation on the computational system 1500 (e.g., using any of a variety of generally available compilers, installation programs, compression/decompression utilities, etc.), then takes the form of executable code.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

That which is claimed:

1. A system comprising:
   an input/output device;
   an electronic data storage;
   a processor communicatively coupled with the electronic data storage and the input/output device, the processor configured to:
   receive coarse-resolution soil moisture data of soil via the input/output device, the coarse-resolution soil moisture data comprising coarse data cells that each represent a soil moisture value of a geographic region having at least one dimension greater than or equal to 1 km;
   store the coarse-resolution soil moisture data in the electronic data storage;
   receive a plurality of fine-resolution supplemental soil moisture data via the input/output device, the fine-resolution supplemental soil moisture data comprising at least one of soil data, vegetation data, topography data, and climate data, the plurality of fine-resolution supplemental soil moisture data comprising data cells that represent a geographic region having at least one dimension less than or equal to 100 meters;
   store the plurality of fine-resolution supplemental soil moisture data in the electronic data storage;
   downscale the coarse-resolution soil moisture data to fine-resolution soil moisture data using a weighted average of soil moisture estimates;
   store the fine-resolution soil moisture data in the electronic data storage; and
   generate and output the fine-resolution soil moisture data as at least one of:
     a matrix of soil moisture values;
     polygons representing different: soil moisture values, locations that are identified as saturated, locations that are identified as ponded, depth of ponded water or runoff, degree of saturation at each location, likelihood of saturation at location, or likelihood of ponding at location;
     the fine-resolution soil moisture data combined with a digital elevation model; or
     the fine-resolution soil moisture data represented as color values on a map,
   wherein the fine resolution soil moisture is estimated from the weighted average of soil moisture estimates by:

$$\theta = \frac{w_G \theta_G + w_L \theta_L + w_R \theta_R + w_A \theta_A}{w_G + w_L + w_R + w_A},$$

where:

$$w_G = \left(\frac{\theta}{\Psi}\right)^{\gamma_v}, w_L = \left(\frac{\theta}{\Lambda}\right)^{\gamma_h}, w_R = \left(\frac{\theta}{\Pi}\right)^{\beta_r}, w_A = \left(\frac{\theta}{\Omega}\right)^{\beta_a},$$

$$\theta_G = \bar{\theta}\frac{DDI}{\Psi}, \theta_L = \bar{\theta}\frac{LFI}{\Lambda}, \theta_R = \bar{\theta}\frac{REI}{\Pi}, \theta_A = \bar{\theta}\frac{AEI}{\Omega},$$

$\bar{\theta}$ represents a spatial-average soil moisture within a coarse-resolution cell, DDI represents a compound soil, vegetation, topography, and/or climate deep drainage index, LFI represents a compound soil, vegetation, topography, and/or climate lateral flow index, REI represents a compound soil, vegetation, topography, and/or climate radiative evapotranspiration (ET) index, AEI represents a compound soil, vegetation, topography, and/or climate aerodynamic ET index, $\Psi$ is a spatial-average DDI within a given coarse-resolution cell, $\Lambda$ is a spatial-average LFI within a given coarse-resolution cell, $\Pi$ is a spatial-average REI within a given coarse-resolution cell, $\Omega$ denotes a spatial-average AEI within a given coarse-resolution cell, $\gamma_v$ is a vertical pore disconnectedness index, $\gamma_h$ is a horizontal pore disconnectedness index, $\beta_r$ is an index that describes an effect of soil moisture on a radiative component of the ET and depends on a soil, vegetation and/or climate, $\beta_a$ is an index that describes an effect of soil moisture on an aerodynamic component of the ET and depends on a soil, vegetation, and/or climate, $$DDI \equiv \phi \left( \frac{1 - \lambda V}{K_{s,v}} \right)^{1/\gamma_h},$$

$\phi$ is a soil porosity that can vary between the fine-resolution grid cells within a coarse-resolution cell, $\lambda$ is a vegetation interception efficiency that is greater than or equal to 0 and less than or equal to 1 and can vary between the fine-resolution grid cells within a coarse-resolution grid cell, V is a fractional vegetation cover that can vary between the fine-resolution grid cells within a coarse-resolution grid cell, $K_{s,v}$ is a soil saturated vertical hydraulic conductivity that can vary between the fine-resolution grid cells within a coarse-resolution grid cell, $$LFI \equiv \phi \left( \frac{1 - \lambda V}{\delta_0 l K_{s,v}} \right)^{1/\gamma_h} \left( \frac{A}{cS^a} \right)^{1/\gamma_h} \left( \frac{K_{min}}{K_{min} - \kappa} \right)^{1/\gamma_h},$$

$\delta_O$ is a thickness of hydrologically active soil layer where topographic curvature is zero that can vary between the fine-resolution grid cells within a coarse-resolution grid cell, l is an anisotropy of soil saturated hydraulic conductivity that can vary between the fine-resolution grid cells within a coarse-resolution grid cell, A is an area upslope from edge of digital elevation model cell that can vary between the fine-resolution grid cells within a coarse-resolution grid cell, C is a length of fine-resolution grid cell edge that can vary between the fine-resolution grid cells within a coarse-resolution grid cell, S is a topographic slope that can vary between the fine-resolution grid cells within a coarse-resolution grid cell, $\varepsilon$ relates horizontal hydraulic gradient to topographic slope and can vary between the fine-resolution grid cells within a coarse-resolution grid cell, $K_{min}$ is a minimum topographic curvature for which the hydrologically active layer is present that can vary between the fine-resolution grid cells within a coarse-resolution grid cell, K is a topographic curvature that can vary between the fine-resolution grid cells within a coarse-resolution grid cell, $$REI \equiv \phi \left( \frac{1 + \alpha}{E_p} \right)^{1/\beta_r} \left( \frac{1}{I_p} \right)^{1/\beta_r} \left( \frac{1 - \lambda V}{\eta V + (1 - V)^\mu} \right)^{1/\beta_r},$$

$\alpha$ is a climate characteristic of a ratio of an aerodynamic term to a radiation term in the calculation of ET that can vary between the fine-resolution grid cells within a coarse-resolution grid cell, $E_p$ is an average potential ET climate characteristic that can vary between the fine-resolution grid cells within a coarse-resolution grid cell, $I_p$ is a ratio of insolation of a topographic surface to that of a horizontal surface at same latitude and date that can vary between the fine-resolution grid cells within a coarse-resolution grid cell, $\eta$ is a vegetation transpiration characteristic related to a portion of transpiration contributed by hydrologically active layer and can vary between the fine-resolution grid cells within a coarse-resolution grid cell, $\mu$ is a vegetation evaporation characteristic related to shading of the ground surface and can vary between the fine-resolution grid cells within a coarse-resolution grid cell, and $$AEI \equiv \phi \left( \frac{1 + \alpha}{E_p \alpha} \right)^{1/\beta_a} \left( \frac{1 - \lambda V}{\eta V + (1 - V)^\mu} \right)^{1/\beta_a}.$$

2. The system according to claim 1, wherein the coarse-resolution soil moisture data comprises soil moisture data collected from a satellite or from weather forecasting models.

3. The system according to claim 1, wherein the soil data comprises one or more soil parameters selected from the group consisting of soil porosity, an anisotropy of a saturated hydraulic conductivity of the soil, a saturated vertical hydraulic conductivity of the soil, a thickness of a hydrologically active layer where a topographic curvature is zero, a minimum topographic curvature for which a hydrologically active layer is present, a parameter representing a percentage of sand in the soil, a parameter representing a percentage of silt in the soil, a parameter representing a percentage of clay in the soil, and a parameter that relates a horizontal hydraulic gradient to topographic slope.

4. The system according to claim 1, wherein the vegetation data comprises one or more vegetation parameters selected from the group consisting of a fractional vegetation cover, an interception efficiency, a fraction transpiration that arises from a hydrologically active layer, a shading efficiency of vegetation, and vegetation type.

5. The system according to claim 1, wherein the climate data comprises one or more climate parameters selected from the group consisting of a potential or reference crop evapotranspiration, precipitation, wind speed, and a ratio of an aerodynamic term to a radiation term.

6. The system according to claim 1, wherein the topographic data comprises one or more topography parameters selected from the group consisting of an elevation, an area that is upslope from an edge of a data cell, a topographic slope, a topographic curvature, a topographic orientation, a ratio of an insolation of a topographic surface to that of a horizontal surface at a same latitude and date.

7. The system according to claim 1, wherein one or more of $W_G$, $W_L$, $W_R$, and $W_A$ are set equal to zero.

8. A method comprising:
receiving coarse-resolution soil moisture data of soil into a computing system, the coarse-resolution soil moisture data comprising data cells that each represent a soil moisture value of a geographic region having at least one dimension greater than or equal to 1 km;
receiving, into the computing system, a plurality of fine-resolution supplemental soil moisture data comprising at least one of soil data, vegetation data, topography data, and climate data, the fine-resolution supplemental soil moisture data comprising data cells that represent a geographic region having at least one dimension less than or equal to 100 meters;
downscaling, with the computing system, the coarse-resolution soil moisture data to fine-resolution soil moisture data using a weighted average of soil moisture estimates;
generating and outputting, with the computing system, the fine-resolution soil moisture data as at least one of:
a matrix of soil moisture values;
polygons representing different: soil moisture values, locations that are identified as saturated, locations that are identified as ponded, depth of ponded water or runoff, degree of saturation at each location, likelihood of saturation at location, or likelihood of ponding at location;
the fine-resolution soil moisture data combined with a digital elevation model; or
the fine-resolution soil moisture data represented as color values
on a map,
wherein the fine resolution soil moisture is estimated from the weighted average of soil moisture estimates by:

$$\theta = \frac{w_G \theta_G + w_L \theta_L + w_R \theta_R + w_A \theta_A}{w_G + w_L + w_R + w_A},$$

where in:

$$w_G = \left(\frac{\bar\theta}{\Psi}\right)^{\gamma_v}, w_L = \left(\frac{\bar\theta}{\Lambda}\right)^{\gamma_h}, w_R = \left(\frac{\bar\theta}{\Pi}\right)^{\beta_r}, w_A = \left(\frac{\bar\theta}{\Omega}\right)^{\beta_a},$$

$$\theta_G = \bar\theta \frac{DDI}{\Psi}, \theta_L = \bar\theta \frac{LFI}{\Lambda}, \theta_R = \bar\theta \frac{REI}{\Pi}, \theta_A = \bar\theta \frac{AEI}{\Omega},$$

$\bar\theta$ represents a spatial-average soil moisture within a coarse-resolution cell,
DDI represents a compound soil, vegetation, topography, and/or climate deep drainage index,
LFI represents a compound soil, vegetation, topography, and/or climate lateral flow index,
REI represents a compound soil, vegetation, topography, and/or climate radiative evapotranspiration (ET) index,
AEI represents a compound soil, vegetation, topography, and/or climate aerodynamic ET index, $\Psi$ is a spatial-average DDI within a given coarse-resolution cell,
$\Lambda$ is a spatial-average LFI within a given coarse-resolution cell,
$\Pi$ is a spatial-average REI within a given coarse-resolution cell,
$\Omega$ denotes a spatial-average AEI within a given coarse-resolution cell,
$\gamma_v$ is a vertical pore disconnectedness index,
$\gamma_h$ is a horizontal pore disconnectedness index,
$\beta_r$ is an index that describes an effect of soil moisture on a radiative component of the ET and depends on a soil, vegetation and/or climate,
$\beta_a$ is an index that describes an effect of soil moisture on an aerodynamic component of the ET and depends on a soil, vegetation, and/or climate, $$DDI \equiv \phi \left(\frac{1 - \lambda V}{K_{s,v}}\right)^{1/\gamma_h},$$

$\phi$ is a soil porosity that can vary between the fine-resolution grid cells within a coarse-resolution grid cell,
$\lambda$ is a vegetation interception efficiency that is greater than or equal to 0 and less than or equal to 1 and can vary between the fine-resolution grid cells within a coarse-resolution grid cell,
V is a fractional vegetation cover that can vary between the fine-resolution grid cells within a coarse-resolution grid cell,
$K_{s,v}$ is a soil saturated vertical hydraulic conductivity that can vary between the fine-resolution grid cells within a coarse-resolution grid cell, $$LFI \equiv \phi \left(\frac{1 - \lambda V}{\delta_0 l K_{s,v}}\right)^{1/\gamma_h} \left(\frac{A}{cS^\alpha}\right)^{1/\gamma_h} \left(\frac{K_{min}}{K_{min} - K}\right)^{1/\gamma_h},$$

$\delta_O$ is a thickness of hydrologically active soil layer where topographic curvature is zero that can vary between the fine-resolution grid cells within a coarse-resolution grid cell,
l is an anisotropy of soil saturated hydraulic conductivity that can vary between the fine-resolution grid cells within a coarse-resolution grid cell,
A is an area upslope from edge of digital elevation model cell that can vary between the fine-resolution grid cells within a coarse-resolution grid cell,
C is a length of fine-resolution grid cell edge that can vary between the fine-resolution grid cells within a coarse-resolution grid cell,
S is a topographic slope that can vary between the fine-resolution grid cells within a coarse-resolution grid cell,
$\varepsilon$ relates horizontal hydraulic gradient to topographic slope and can vary between the fine-resolution grid cells within a coarse-resolution grid cell,
$K_{min}$ is a minimum topographic curvature for which the hydrologically active layer is present that can vary between the fine-resolution grid cells within a coarse-resolution grid cell,
K is a topographic curvature that can vary between the fine-resolution grid cells within a coarse-resolution grid cell, $$REI \equiv \phi \left(\frac{1+\alpha}{E_p}\right)^{1/\beta_r} \left(\frac{1}{I_p}\right)^{1/\beta_r} \left(\frac{1-\lambda V}{\eta V + (1-V)^\mu}\right)^{1/\beta_r},$$

α is a climate characteristic of a ratio of an aerodynamic term to a radiation term in the calculation of ET that can vary between the fine-resolution grid cells within a coarse-resolution grid cell, $E_p$ is an average potential ET climate characteristic that can vary between the fine-resolution grid cells within a coarse-resolution grid cell, $I_p$ is a ratio of insolation of a topographic surface to that of a horizontal surface at same latitude and date that can vary between the fine-resolution grid cells within a coarse-resolution grid cell, η is a vegetation transpiration characteristic related to a portion of transpiration contributed by hydrologically active layer and can vary between the fine-resolution grid cells within a coarse-resolution grid cell, μ is a vegetation evaporation characteristic related to shading of the ground surface and can vary between the fine-resolution grid cells within a coarse-resolution grid cell, and $$AEI \equiv \phi \left(\frac{1+\alpha}{E_p \alpha}\right)^{1/\beta_a} \left(\frac{1-\lambda V}{\eta V + (1-V)^\mu}\right)^{1/\beta_a}.$$

9. The method according to claim 8, wherein the coarse-resolution soil moisture data comprises soil moisture data collected from a satellite or from weather forecasting models.

10. The method according to claim 8, wherein the soil data comprises one or more soil parameters selected from the group consisting of soil porosity, an anisotropy of a saturated hydraulic conductivity of the soil, a saturated vertical hydraulic conductivity of the soil, a thickness of a hydrologically active layer where a topographic curvature is zero, a minimum topographic curvature, and a parameter that relates a horizontal hydraulic gradient to topographic slope.

11. The method according to claim 8, wherein the vegetation data comprises one or more vegetation parameters selected from the group consisting of a fractional vegetation cover, an interception efficiency, and vegetation type.

12. The method according to claim 8, wherein the climate data comprises one or more climate parameters selected from the group consisting of an average potential evapotranspiration and a ratio of an aerodynamic term to a radiation term.

13. The method according to claim 8, wherein the soil data comprises one or more topography parameters selected from the group consisting of an area that is upslope from an edge of a data cell, a topographic slope, a topographic curvature, a ratio of an insolation of a topographic surface to that of a horizontal surface at a same latitude and date.

14. One or more non-transitory computer-readable media storing one or more programs that are configured, when executed, to cause one or more processors to execute a method comprising:

receiving coarse-resolution soil moisture data, the coarse-resolution soil moisture data comprising data cells that each represent a soil moisture value of a geographic region having at least one dimension greater than or equal to 1 km;

receiving a plurality of fine-resolution supplemental soil moisture data comprising at least one of soil data, vegetation data, topography data, and climate data, the fine-resolution supplemental soil moisture data comprising data cells that represent a geographic region having at least one dimension less than or equal to 100 meters;

determining a weighted average of soil moisture estimates from the fine-resolution supplemental soil moisture data;

downscaling the coarse-resolution soil moisture data to fine-resolution soil moisture data using a weighted average of soil moisture estimates; and generating and outputting the fine-resolution soil moisture data as at least one of:

a matrix of soil moisture values;

polygons representing different: soil moisture values, locations that are identified as saturated, locations that are identified as ponded, depth of ponded water or runoff, degree of saturation at each location, likelihood of saturation at location, or likelihood of ponding at location;

the fine-resolution soil moisture data combined with a digital elevation model; or the fine-resolution soil moisture data represented as color values on a map, wherein the fine resolution soil moisture is estimated from the weighted average of soil moisture estimates by:

$$\theta = \frac{w_G \theta_G + w_L \theta_L + w_R \theta_R + w_A \theta_A}{w_G + w_L + w_R + w_A},$$

where in:

$$w_G = \left(\frac{\overline{\theta}}{\Psi}\right)^{\gamma_v}, w_L = \left(\frac{\overline{\theta}}{\Lambda}\right)^{\gamma_h}, w_R = \left(\frac{\overline{\theta}}{\Pi}\right)^{\beta_r}, w_A = \left(\frac{\overline{\theta}}{\Omega}\right)^{\beta_a},$$

$$\theta_G = \overline{\theta}\frac{DDI}{\Psi}, \theta_L = \overline{\theta}\frac{LFI}{\Lambda}, \theta_R = \overline{\theta}\frac{REI}{\Pi}, \theta_A = \overline{\theta}\frac{AEI}{\Omega},$$

$\overline{\theta}$ represents a spatial-average soil moisture within a coarse-resolution cell, DDI represents a compound soil, vegetation, topography, and/or climate deep drainage index, LFI represents a compound soil, vegetation, topography, and/or climate lateral flow index, REI represents a compound soil, vegetation, topography, and/or climate radiative evapotranspiration (ET) index, AEI represents a compound soil, vegetation, topography, and/or climate aerodynamic ET index, Ψ is a spatial-average DDI within a given coarse-resolution cell, Λ is a spatial-average LFI within a given coarse-resolution cell, Π is a spatial-average REI within a given coarse-resolution cell, Ω denotes a spatial-average AEI within a given coarse-resolution cell, $\gamma_v$ is a vertical pore disconnectedness index, $\gamma_h$ is a horizontal pore disconnectedness index, $\beta_r$ is an index that describes an effect of soil moisture on a radiative component of the ET and depends on a soil, vegetation and/or climate, $\beta_a$ is an index that describes an effect of soil moisture on an aerodynamic component of the ET and depends on a soil, vegetation, and/or climate, $$DDI \equiv \phi \left( \frac{1 - \lambda V}{K_{s,v}} \right)^{1/\gamma_h},$$

$\phi$ is a soil porosity that can vary between the fine-resolution grid cells within a coarse-resolution grid cell, $\lambda$ is a vegetation interception efficiency that is greater than or equal to 0 and less than or equal to 1 and can vary between the fine-resolution grid cells within a coarse-resolution grid cell, V is a fractional vegetation cover that can vary between the fine-resolution grid cells within a coarse-resolution grid cell, $K_{s,v}$ is a soil saturated vertical hydraulic conductivity that can vary between the fine-resolution grid cells within a coarse-resolution grid cell, $$LFI \equiv \phi \left( \frac{1 - \lambda V}{\delta_0 l K_{s,v}} \right)^{1/\gamma_h} \left( \frac{A}{cS^a} \right)^{1/\gamma_h} \left( \frac{K_{min}}{K_{min} - \kappa} \right)^{1/\gamma_h},$$

$\delta$ is a thickness of hydrologically active soil layer where topographic curvature is zero that can vary between the fine-resolution grid cells within a coarse-resolution grid cell, l is an anisotropy of soil saturated hydraulic conductivity that can vary between the fine-resolution grid cells within a coarse-resolution grid cell, A is an area upslope from edge of digital elevation model cell that can vary between the fine-resolution grid cells within a coarse-resolution grid cell, C is a length of fine-resolution grid cell edge that can vary between the fine-resolution grid cells within a coarse-resolution grid cell, S is a topographic slope that can vary between the fine-resolution grid cells within a coarse-resolution grid cell, $\varepsilon$ relates horizontal hydraulic gradient to topographic slope and can vary between the fine-resolution grid cells within a coarse-resolution grid cell, $K_{min}$ is a minimum topographic curvature for which the hydrologically active layer is present that can vary between the fine-resolution grid cells within a coarse-resolution grid cell, K is a topographic curvature that can vary between the fine-resolution grid cells within a coarse-resolution grid cell, $$REI \equiv \phi \left( \frac{1 + \alpha}{E_p} \right)^{1/\beta_r} \left( \frac{1}{I_p} \right)^{1/\beta_r} \left( \frac{1 - \lambda V}{\eta V + (1 - V)^\mu} \right)^{1/\beta_r},$$

$\alpha$ is a climate characteristic of a ratio of an aerodynamic term to a radiation term in the calculation of ET that can vary between the fine-resolution grid cells within a coarse-resolution grid cell, $E_p$ is an average potential ET climate characteristic that can vary between the fine-resolution grid cells within a coarse-resolution grid cell, $I_p$ is a ratio of insolation of a topographic surface to that of a horizontal surface at same latitude and date that can vary between the fine-resolution grid cells within a coarse-resolution grid cell, $\eta$ is a vegetation transpiration characteristic related to a portion of transpiration contributed by hydrologically active layer and can vary between the fine-resolution grid cells within a coarse-resolution grid cell, $\mu$ is a vegetation evaporation characteristic related to shading of the ground surface and can vary between the fine-resolution grid cells within a coarse-resolution grid cell, and $$AEI \equiv \phi \left( \frac{1 + \alpha}{E_p \alpha} \right)^{1/\beta_a} \left( \frac{1 - \lambda V}{\eta V + (1 - V)^\mu} \right)^{1/\beta_a}.$$

* * * * *